(12) United States Patent
Sun et al.

(10) Patent No.: US 11,992,493 B1
(45) Date of Patent: May 28, 2024

(54) USE OF COMPOUND OR PHARMACEUTICAL DERIVATIVE THEREOF IN INHIBITING CaMK2G PROTEIN ACTIVITY

(71) Applicant: Liangdan Sun, Hefei (CN)

(72) Inventors: Liangdan Sun, Hefei (CN); Yirui Wang, Hefei (CN); Zhuo Li, Hefei (CN); Weiwei Chen, Hefei (CN); Qi Zhen, Hefei (CN)

(73) Assignee: Liangdan Sun, Hefei (CN)

( * ) Notice: Subject to any disclaimer, the term of this patent is extended or adjusted under 35 U.S.C. 154(b) by 0 days.

(21) Appl. No.: 18/083,395

(22) Filed: Dec. 16, 2022

(30) Foreign Application Priority Data

Oct. 25, 2022 (CN) .......................... 202211316391.9

(51) Int. Cl.
*A61K 31/55* (2006.01)
*A61P 17/06* (2006.01)

(52) U.S. Cl.
CPC .............. *A61K 31/55* (2013.01); *A61P 17/06* (2018.01)

(58) Field of Classification Search
CPC ................................ A61K 31/55; A61P 17/06
See application file for complete search history.

(56) References Cited

U.S. PATENT DOCUMENTS

2014/0235618 A1* 8/2014 Cheung .................. A61K 31/55
514/214.02

FOREIGN PATENT DOCUMENTS

| WO | WO 2013/003825 | * | 1/2013 |
| WO | WO 2022/208146 | * | 10/2022 |

* cited by examiner

*Primary Examiner* — Shobha Kantamneni

(57) ABSTRACT

A use of a compound or a medicinal derivative thereof in inhibiting calcium/calmodulin-dependent protein kinase type II gamma (CaMK2γ) protein activity is provided, and belongs to the technical field of protein inhibitors. Compared with traditional broad-spectrum immunomodulators, the compound has a strong targeting effect, and is more accurate, rapid, effective, safe, and stable. Moreover, the compound has a strong binding force with human-derived CaMK2γ protein and mouse-derived CaMK2γ protein, and binding constants are KD=$2.54 \times 10^{-5}$M and KD=$6.84 \times 10^{-5}$ M respectively. Compared with traditional biological inhibitors, the compound has advantages of easy storage, stable activity, small molecular weight, lower production cost and easy absorption.

11 Claims, 14 Drawing Sheets

USE OF COMPOUND OR PHARMACEUTICAL DERIVATIVE THEREOF IN INHIBITING CaMK2G PROTEIN ACTIVITY

TECHNICAL FIELD

The disclosure relates to the technical field of protein inhibitors, and more particularly to a use/application of a compound or a pharmaceutical derivative thereof in inhibiting calcium/calmodulin-dependent protein kinase type II gamma (CaMK2γ, also referred to as CaMK2G) protein activity.

BACKGROUND

Psoriasis is a global, refractory, high incidence rate inflammatory-immune disease, which cannot be completely cured under a current medical level. There are many clinical treatments for psoriasis, most of which attempt to alleviate symptoms through extensive inhibition of an immune system, such as uses of hormones and immunosuppressants, and uses of some physical therapy and traditional Chinese drug. However, broad-spectrum symptomatic treatment is often ineffective, which is very easy to cause repeated illness or other system damage. In recent years, the development of precision drug for psoriasis has made up for shortcomings of traditional treatment regimens to a certain extent, and many biological agents have been developed to target effector molecules downstream of an inflammatory pathway of psoriasis, such as interleukin-17 (IL-17), tumor necrosis factor alpha (TNF-α), and interleukin-23 (IL-23), in an attempt to eliminate a phenotype of psoriasis.

Compared with the traditional treatment regimens, the biological agents can increase a cure rate of patients with psoriasis to varying degrees over a period of time, with longer dosing interval and greater compliance. However, it has same disadvantages as the traditional treatment regimens. At present, all biological agents for psoriasis on the market are still symptomatic treatments that fundamentally reduce the phenotype by blocking efficacy of downstream effector molecules. If uses of the biological agents are stopped for more than half a year, the risk of psoriasis recurrence will be greatly increased. In addition, the biological agents are expensive, because of the need for long-term maintenance of medication, if the effect is weakened halfway, a variety of biological agents should be used in combination, which brings a greater economic burden to patients.

To sum up, drugs currently used in the treatment of psoriasis can be divided into two main types including broad-spectrum immunomodulatory drugs and targeted drugs. The long-term effect of traditional broad-spectrum immunomodulatory drugs is not ideal. The targeted drugs represented by biological agents make up for lacks of efficacy of traditional drugs to a certain extent, but the biological agents are expensive and have relatively high applicable standards. There are few other types of targeted drugs (natural small molecules or artificial compounds) for psoriasis on the market, and almost all of them target a downstream effector pathway in the pathogenesis of psoriasis, which has a weak impact on a key cytokine IL-17 and its upstream initiation pathway. Compared with the treatment that interferes with factors of an upstream of the inflammatory pathway of psoriasis, the long-term effect of this symptomatic treatment may not be good.

Therefore, it is imperative to develop new drugs that complement advantages of traditional treatment and the biological agents, not only to make up for the shortcomings of the above drugs, but also to take into account the effectiveness, targeting, economy, safety, compliance of drugs.

SUMMARY

In view of the above problems, the disclosure aims to provide a compound or a pharmaceutical derivative thereof in inhibiting calcium/calmodulin-dependent protein kinase type II gamma (CaMK2γ, also referred to as CaMK2G) protein activity, the compound can inhibit the CaMK2γ protein activity, so as to significantly inhibit the production of interleukin-17A (IL-17A), IL-17F, tumor necrosis factor alpha (TNF-α), IL23A, reduce the proportion of IL-17A positive cells in dermis γδT cells of imiquimod (IMQ)-induced mice, and can significantly alleviate inflammatory phenotypes (i.e., reduce psoriatic symptoms) of IMQ mice. That is, the compound of the disclosure can be used as a drug to treat psoriasis to reduce psoriasis-like lesions induced by IMQ (i.e., Psoriasis Area and Severity Index abbreviated PASI score is reduced).

In order to achieve the above purpose, the disclosure can use the following technical solutions.

In an aspect, the disclosure provides a use of the compounds or the pharmaceutical derivative thereof in inhibiting CaMK2γ protein activity. A structure of the compound is shown in a formula I, a molecular formula of the compound is $C_{19}H_{21}N_3O$ with a molecular weight of 307.39, and the formula I is expressed as follows:

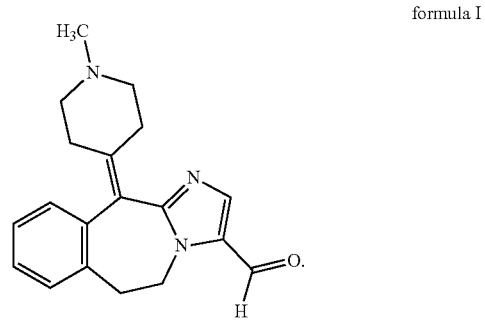 [SMILES: CN1CCC(=C2c3ccccc3CCn3c(C=O)cnc32)CC1]

formula I

In another aspect, the disclosure provides a use of one of a compound and a pharmaceutical derivative of the compound in preparing a drug for inhibiting CaMK2γ protein activity.

In still another aspect, the disclosure provides a pharmaceutical composition for treating psoriasis, at least including a compound as shown in a formula I; and/or a pharmaceutical carriers a and/or a diluent; and the formula I is expressed as follows:

formula I

[Chemical structure of Alcaftadine]

The beneficial effects of the disclosure include:

(1) the compound I (also referred to as Alcaftadine, corresponding to compound library No.: T2533) in the disclosure is an active small molecule targeting CaMK2γ protein, and the compound or the drug prepared by the compound is used for treating psoriasis. Compared with traditional broad-spectrum immunomodulators, the compound I has a stronger targeting effect, and is more accurate, rapid, effective, safe, and stable. Furthermore, the compound I has a strong binding force with human-derived CaMK2γ protein and mouse-derived CaMK2γ protein, and binding constants are as high as $2.54 \times 10^{-5}$ M and $6.84 \times 10^{-5}$ M respectively.

(2) a target point of the compound and the prepared drug thereof for binding inhibition in psoriasis is located at upstream of a CaMK2γ pathway. Compared with the traditional biological inhibitors (where the biological inhibitors all act on a middle and a downstream psoriatic immune-inflammatory pathway, belong to symptomatic treatment, have unstable maintenance on the treatment effect, and greatly increase a recurrence rate of almost all the biological inhibitors after stopping medication for half a year), a blocking level to inflammatory factors is higher, and the long-term effect is more considerable than that of the biological inhibitors. Moreover, most of traditional biological agents are system injection drugs, which are very easy to affect other systems. However, the compound in the disclosure is easy to absorb for external use, which can avoid many side effects caused by system administration, and have advantages of high safety, wide applicable population, convenient administration and good compliance.

(3) The compound of the disclosure is a white crystal small molecule in a liquid form or dissolved in a colorless solvent in a colorless and clear state, and can increase applicability and aesthetics of external use on the skin after being prepared into the drug.

BRIEF DESCRIPTION OF DRAWINGS

Specifically, in FIG. 1, portion A shows a NewCartoon model and portion B shows a molecular surface area. In FIG. 6, portion A illustrates a composite structure formed with T2533 and human-derived CaMK2γ protein and an interaction between T2533 and CaMK2γ protein in a pocket 1 region of CaMK2γ protein, where a surface area of the CaMK2γ protein is represented in orange, T2533 is represented in green, and R297, R298, and K301 form a hydrogen bond interaction with T2533. Portion B illustrates a chemical structural formula of T2533. Portion C illustrates a two-dimensional (2D) interaction pattern between T2533 and important targeting interacting amino acids, where R297, R298, and K301 form the hydrogen bond interaction with T2533.

DETAILED DESCRIPTION OF EMBODIMENTS

Figure 1:
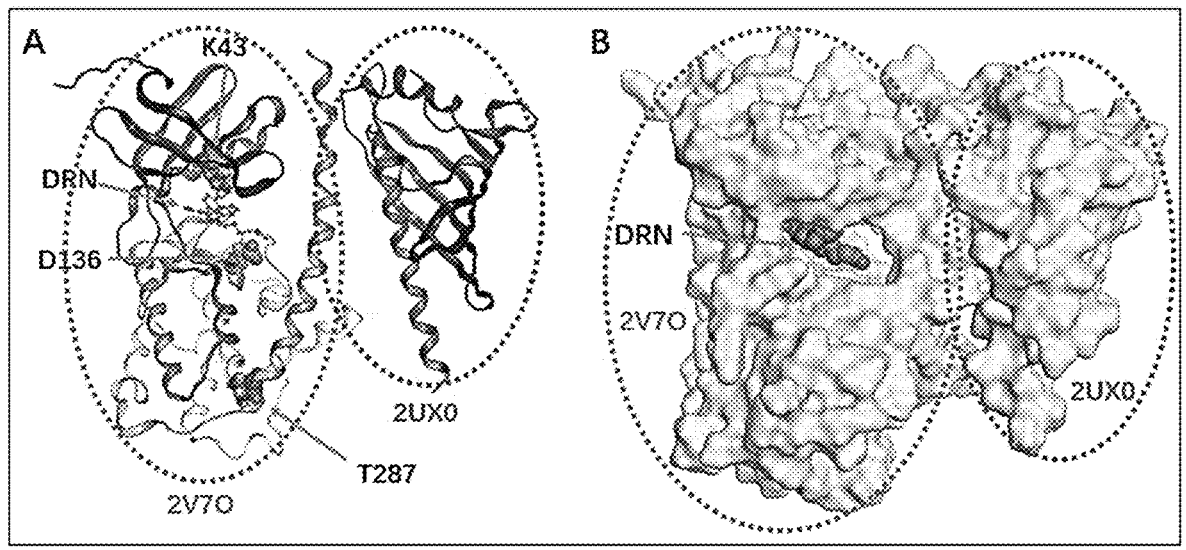
FIG. 1 illustrates a schematic crystal structure of a calcium/calmodulin-dependent protein kinase type II gamma (CaMK2γ, also referred to as CaMK2G) protein.

Illustrated embodiments are intended to better illustrate the disclosure and are not intended to limit the scope of the disclosure to the illustrated embodiments. Therefore, non-essential modifications and adjustments of implementation solutions by those skilled in the art according to the above disclosure still belong to the protection scope of the disclosure.

Terms used herein are used only to describe specific embodiments and are not intended to limit the disclosure. Expressions in a singular may include expressions in a plural unless they have a significantly different meaning in the context. As used herein, it should be understood that terms such as "include", "have", "contain" are intended to indicate the presence of features, numbers, operations, components, parts, elements, materials or combinations. The terms of the disclosure are disclosed in the specification and are not intended to exclude the possibility that one or more other features, numbers, operations, components, parts, elements, materials or combinations thereof may be present or may be added. As used here, "/" may be interpreted as "and" or "or" depending on the situation.

An embodiment of the disclosure provides a use of one of a compound or a pharmaceutical derivative thereof in inhibiting calcium/calmodulin-dependent protein kinase type II gamma (CaMK2γ, also referred to as CaMK2G) protein activity. The compound can be used as a drug to treat psoriasis, which can significantly reduce interleukin-17A (IL-17A)$^+$ cells in dermal γδT subsets in IMQ-induced mouse skin lesions, significantly alleviate inflammatory phenotypes of IMQ-induced mice. A structure of the compound is shown in a formula I as follows, a molecular formula of the compound is $C_{19}H_{21}N_3O$ with a molecular weight of 307.39, and the formula I is expressed as follows:

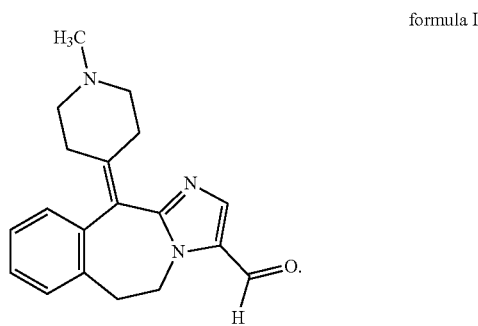 [SMILES: CN1CCC(=C2c3ccccc3CCn3c(C=O)cnc32)CC1]

formula I

Single cell transcriptome sequencing, assay for transposase-accessible chromatin with high-throughput (ATAC) sequencing, transcriptomics, genomics and other multi-omics researches of psoriatic patients and imiquimod (IMQ) induced psoriatic mice show that on the basis of genetics, a variety of technologies of function assessment are used to analyze the susceptible gene CaMK2γ at levels of protein, cell animal model and tissue samples, and results show that CaMK2γ in skin is mainly expressed in sympathetic nerve, CaMK2γ promotes T6T cells to produce IL-17 through a pathway of skin sympathetic nerve-norepinephrine (NE)-γδT-adrenoceptor beta 2 (ADRB2)-p38, thereby aggravating the inflammatory response of psoriasis. The CaMK2γ pathway has been proved to play a crucial role in the occurrence and aggravation of psoriasis, and regulating the activity of the CaMK2γ pathway can control the psoriasis-like inflammatory phenotype of an IMQ-induced mouse model. CaMK2γ is an upstream initiator of the pathway, and blocking the ability of the CaMK2γ protein to activate downstream proteins in psoriasis can efficiently block the effect of the pathway, in principle with a more powerful and durable efficacy than eliminating only the enforcement factor IL-17. Considering that in the traditional systemic biotherapy, blocking upstream molecules may cause other system abnormalities affected by the related pathway.

An inhibitor T2533 with inhibitory activity is obtained by screening from Chemdiv and TargetMol® databases containing 1.5 million compounds based on virtual screening and experimental verification methods. and that affinity, the druggability score, the structural diversity and other properties of the conformations of the compounds and the human-derived CaMK2γ protein are further calculated, so that the T2533 is finally determined to be the inhibitor of the human-derived CaMK2γ protein through experimental verification, namely the compound shown as the formula I.

In addition, pharmaceutical derivatives of the compound refer to compounds obtained by retaining a mother nucleus structure and changing of the structure on the basis of the mother nucleus structure. The compounds obtained by changing the structure can retain the efficacy of inhibiting the activity of CaMK2γ protein, improve the activity of the compound, and improve the pharmacokinetic properties.

In some specific embodiments, in the above use, the compound is in a form of a pharmaceutical salt. It should be noted that, in the actual drug application, in order to ensure the convenience of drug application and storage, the compound can be prepared into the form of a pharmaceutical salt.

In some specific embodiments, in the above use, the above compound is in a form of a pharmaceutical acid addition salt. It should be noted that the above compound is prepared in the form of pharmaceutical salt, preferably in the form of pharmaceutical acid addition salt. The preparation is fast and convenient. Of course, other forms of salt formation are not excluded.

Another embodiment of the disclosure provides a use of one of the compound and pharmaceutical derivatives thereof in preparing a drug for inhibiting CaMK2γ protein activity.

In some specific embodiments, in the above use, the drug for inhibiting the CaMK2γ protein activity is specifically used to inhibit the CaMK2γ protein activity in psoriatic tissues. Specifically, as mentioned above, on the basis of genetics, a variety of technologies of function assessment are used to analyze the susceptible gene CaMK2γ at levels of protein, cell animal model and tissue samples, and results show that CaMK2γ in skin is mainly expressed in sympathetic nerve, CaMK2γ promotes T6T cells to produce IL-17 through a pathway of skin sympathetic nerve-NE-γδT-ADRB2-p38, thereby aggravating the inflammatory response of psoriasis. It indicates that the above compound is more targeted to psoriasis and has lower side effects.

In some specific embodiments, in the above use, the compound is in a form of a pharmaceutical salt. As mentioned above, in order to ensure the convenience of drug application and storage, the compound can be prepared into the form of pharmaceutical salt. The form of pharmaceutical acid addition salt is preferred.

In some specific embodiments, in the above use, a dosage form of the drug for inhibiting the CaMK2γ protein activity is a capsule, a tablet, an oral preparation, a microcapsule preparation, an injection, a suppository, a spray, or an ointment. Specifically, those skilled in the art can select an appropriate dosage form according to the route of administration and the object of administration.

Still another embodiment of the disclosure provides a pharmaceutical composition for treating psoriasis, which at least includes the compound shown in the formula I; and/or a pharmaceutical carrier and/or a diluent. The formula I is expressed as follows:

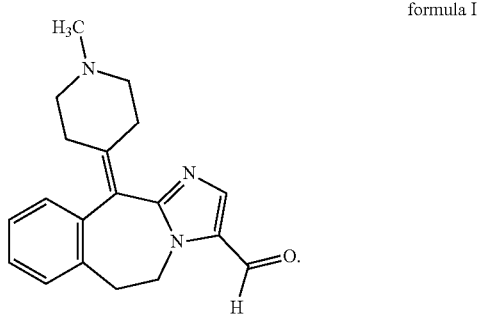 [SMILES: CN1CCC(=C2c3ccccc3CCn3c(C=O)cnc32)CC1]

formula I

In some specific embodiments, in the above pharmaceutical composition, the above pharmaceutical carrier and/or the diluent are applicable to any of a solution dosage form, a colloidal solution dosage form, an emulsion, a suspension dosage form, a gas dispersion dosage form, a particle dispersion dosage form, and a solid dispersion dosage form.

It should also be noted that the compound shown in the formula I above can be used in combination with other drugs for treating of psoriasis to achieve better therapeutic effects, such as combined use with biological agents targeting downstream molecules IL-17 or IL-23, which can reduce the minimum effective dose of biological agents, reduce the interference of biological agents on other systems to a certain extent, and achieve more stable and safer effect. In some specific embodiments, a dosage of an active ingredient of the compound used in the medicament for treating psoriasis is 5 milligrams per kilogram (mg/kg).

In the disclosure, based on molecular docking scores, the docking results of 43083 compounds from Chemdiv and TargetMol® databases are retained, including 19 compounds (Chemdiv) with affinity less than −16 kilocalories per mole (kcal/mol). The compounds are evaluated, scored, and screened by calculating and analyzing properties of small molecule compounds, such as water solubility (Log S) at 7.4 pH, octanol/water distribution coefficient (Log P), molecular weight, molecular flexibility, hydrogen bond property, topological polar surface area (TPSA), cytochrome P450 family 2 subfamily C member 9 (CYP2C9) enzyme degradation level, human ether-à-go-go-related gene (hERG) inhibition rate, human intestinal absorption (HIA), drug-drug interaction risk (2D6) and other indexes, and a scoring function for oral central nervous system drugs (also referred to as CNS DrugScore) and Lipinski's rule of five (also referred to as Lipinski Score). Among the compounds, there are 10,726 compounds can pass through the blood-brain barrier (BBB), and their CNS druggability scores are mostly less than 0.4, indicating that there is still room for optimization of druggability.

Then, compounds from a natural product library and a drug library with affinity less than −11.5 kcal/mol and from the ChemDiv with affinity less than −14 kcal/mol are selected and have a Lipinski's rule of five score greater than 0.5, a CNS score greater than 0.1, and a BBB score greater than −1, finally 678 compounds are obtained. On the basis of 678 compounds, compounds with poor druggability are further screened, such as compounds with TPSA>70, compounds with poor intestinal absorption (HIA Category —), compounds easily hydrolyzed by metabolic enzymes (2D6 value=very high), and compounds that may have cardiotoxicity (hERG>7), and compounds with the molecular weight greater than 500, and finally 570 compounds are retained. Based on the structural similarity (threshold=0.7), the 570 compounds are clustered into 70 groups. In each group, compounds with high affinity are selected to form compounds with high affinity and diversity, totaling 293 compounds.

The above 293 compounds are the final compounds screened in this project, and their indexes have met the requirements of druggability. To further identify possible active compounds, subsequent activity tests are conducted on the compounds with scoring functions top100 (ChemDiv database) and top30 (TargetMol® database). 130 (TOP30, TOP100) small molecule inhibitors of CaMK2γ are screened according to the order of affinity, and the compounds with inhibitory effect and higher safety are screened out by using ADP-Glo™ Kinase Assay+CaMK2γ Kinase Enzyme System (Promega #V9201). The method specifically includes the following steps.

(1) Specific Process of Selecting a Crystal Structure of CaMK2γ Protein

The crystal structure of CaMK2γ has been resolved (2V7O, 2UX0), revealing the three-dimensional (3D) conformation of a protein catalytic domain and structures of CaMK2γ in states of tetradecmer and physiological dodecamer (as shown in FIG. 1). 2UX0 resolves a hexamer structure of R395-A521 fragment of CaMK2γ, and the fragment has no deletion or mutation. 2V70 resolves a 3D structure of A5-G302 fragment of CaMK2γ, the structure has a mutation site S36P, and a spatial position of A24 site is uncertain. Since the crystal structure only analyzes the 3D structure of some fragments, AlphaFold is used to construct a full-length structure model of human CaMK2γ, the structure of the model is highly consistent with the crystal structure (Root Mean Square Deviation abbreviated RMSD: 0.45 to 2UX0; RMSD: 1.587 to 2V70). Therefore, in the subsequent inhibitor screening work, the AlphaFold model is used for the 3D structure model of CaMK2γ. After structural optimization and protonation, its structure is used as a receptor file for screening.

(2) Specific Process of Selecting Binding Sites

Molecular Operating Environment (MOE)-site finder is used to determine pocket1 on the target as the docking region for this virtual screening. The volume of the docking region is an atom-sized space, including 110 atoms with relatively strong hydrophobicity, an adenosine triphosphate (ATP) binding site K43 and an active site D136. An apopd2receiver tool of OpenEye (Release 3.2.0.2) is used to process and generate the virtual screened receptor file, and the molecular docking region is defined with a length, a width, and a height of 32 angstroms (Å)*28.67 Å*21.67 Å, the volume of 19875 cubic angstroms ($Å^3$), and the volume of an inner contour of 1648 $Å^3$.

Figure 2:
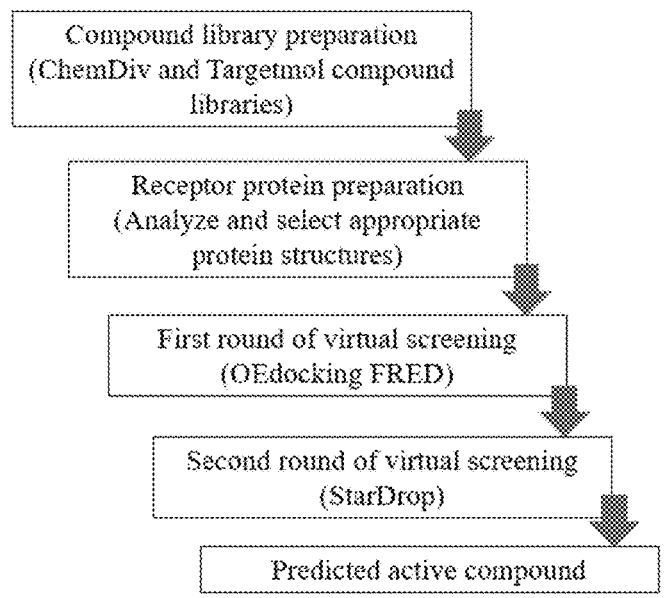
FIG. 2 illustrates a schematic flowchart of a virtual screening.

(3) Specific Process of Determining a Process of Computer Virtual Screening (See FIG. 2) and a Small-Molecule Compound Library, and Selecting and Preparing a Target Protein The virtual screening process is as follows. In terms of hardware, Dell T7910 workstation, Ubuntu kylin 15.10 operating system, 40 core CPU, 64G memory, 512G solid state disk and 4T storage space are used. The virtual screening software is FRED (Ver 3.2.0.2), which is a software used for affinity screening. Receptor file is the 3D structure of CaMK2γ based on the AlphaFold model (also referred to as AF model) and the determined screening area. The compound library is the processed ChemDiv database, the natural product library of TargetMol®, and an approved drug library L1000. The running parameter is -save_component_scores, the option is true, -hitlist_size is set to 30000, -docked_molecule_file is selected sdf format, and other parameters are used default parameters.

The ChemDiv database, the natural product library of TargetMol® and the approved drug library L1000 are the databases for this virtual screening. The ChemDiv database contains 1535478 compounds, the natural product library contains 19746 compounds, and the approved drug library contains 2040 compounds. The plug-in omega2 (Ver 3.0.1.2) in the OpenEye software is used to generate the multi-conformational structure of each small molecule compound in the compound library, each small molecule generates about 50 conformations on average.

Preparation of target protein is as follows. Based on the 3D model of human-derived CaMK2G constructed by AlphaFold, the receptor file is generated through protonation processing and structural optimization, and the pocket 1 region containing the ATP binding site and the active site on the target is determined by the MOE-site finder as the docking region of this virtual screening. The apopd2receiver tool of Openeye (Release 3.2.0.2) is used to process and generate the receptor file of virtual screening, which is used for the protein structure file of virtual screening.

(4) Specific Process of Virtual Screening Calculation (a), affinity calculation by the virtual screening software FRED (Ver 3.2.0.2) software for affinity screening. The software is used to calculate the affinity of different conformations of each compound with CaMK2γ. The interaction of the docking region of each conformation with CaMK2γ is calculated through a rigid-body docking algorithm, and Chemgauss4 is used as the force field to calculate the affinity. Based on the molecular docking score, the docking results of 43083 compounds are retained from Chemdiv and TargetMol databases, including 19 compounds with affinity less than −16 kcal/mol (chemdiv);

(b), calculation and screening of druggability of small molecule compounds. The water solubility (Log S), octanol/water distribution coefficient (Log P), molecular weight, molecular flexibility, hydrogen bond property, TPSA, CYP2C9 enzyme degradation level, hERG inhibition rate, HIA, drug-drug interaction risk (2D6) and other indexes, and a scoring function for oral central nervous system drugs (also referred to as CNS DrugScore) and Lipinski's rule of five (also referred to as Lipinski Score) of the compounds are calculated. Compounds that can penetrate a blood-brain barrier are retained, totaling 10,726 compounds, most of which had CNS DrugScore scores less than 0.4. Then, compounds from a natural product library and a drug library with affinity less than −11.5 kcal/mol and from the ChemDiv with affinity less than −14 kcal/mol are selected and have a Lipinski's rule of five score greater than 0.5, a CNS score greater than 0.1, and a BBB score greater than −1, finally 678 compounds are obtained. On the basis of 678 compounds, compounds with poor druggability are further screened, such as compounds with TPSA>70, compounds with poor intestinal absorption (HIA Category —), compounds easily hydrolyzed by metabolic enzymes (2D6 value=very high), and compounds that may have cardiotoxicity (hERG>7), and compounds with the molecular weight greater than 500, and finally 570 compounds are retained.

(c), Cluster analysis of compounds based on structural similarity. The structural similarity threshold is 0.7, the obtained 570 compounds are clustered into 70 groups. In each group, compounds with high affinity are selected to form compounds with high affinity and diversity, totaling 293 compounds.

The above 293 compounds are the final compounds screened in this project, and their indexes have met the requirements of druggability. To further identify possible active compounds, 100 compounds are selected from Chemdiv database as potential CaMK2γ inhibitors, as shown in Table 1.

TABLE 1

100 potential CaMK2γ inhibitors

| ID | Lipinski Rule_Score | CNS Score | Docking Score | MW | HBD | HBA | TPSA |
|---|---|---|---|---|---|---|---|
| V015-0188 | 0.50080001 | 0.007132 | −17.059999 | 471.60001 | 1 | 4 | 48.990002 |
| V015-0130 | 0.8017 | 0.01433 | −16.32 | 415.5 | 1 | 4 | 48.990002 |
| V013-6529 | 0.5679 | 0.02463 | −16.110001 | 397.5 | 1 | 4 | 48.990002 |
| 3341-3817 | 0.70889997 | 0.02832 | −16.09 | 351.39999 | 2 | 3 | 44.470001 |

TABLE 1-continued 100 potential CaMK2γ inhibitors

| ID | Lipinski Rule_Score | CNS Score | Docking Score | MW | HBD | HBA | TPSA |
|---|---|---|---|---|---|---|---|
| 5511-0312 | 0.79549998 | 0.01715 | −15.99 | 352.39999 | 3 | 3 | 51.810001 |
| S610-0103 | 1 | 0.2525 | −15.74 | 360.39999 | 0 | 4 | 40.619999 |
| H025-0422C | 1 | 0.1584 | −14.77 | 368.5 | 0 | 4 | 33.950001 |
| S647-0218 | 1 | 0.2114 | −14.58 | 363.5 | 0 | 4 | 36.439999 |
| S994-0823 | 1 | 0.1263 | −14.49 | 399.5 | 0 | 6 | 57 |
| P168-0301 | 1 | 0.2039 | −14.49 | 333.39999 | 0 | 4 | 38.130001 |
| C151-0106 | 1 | 0.1472 | −14.32 | 367.39999 | 0 | 4 | 46.09 |
| J042-0823 | 1 | 0.1044 | −14.27 | 374.39999 | 1 | 4 | 49.41 |
| V027-0642 | 0.99599999 | 0.123 | −14.27 | 302.39999 | 0 | 2 | 16.129999 |
| V031-0368 | 0.99769998 | 0.1131 | −14.26 | 314.39999 | 0 | 2 | 16.129999 |
| E822-2182 | 0.99989998 | 0.1849 | −14.24 | 319.39999 | 2 | 4 | 57.779999 |
| SC13-0043 | 1 | 0.1487 | −14.2 | 369.5 | 0 | 5 | 53.509998 |
| V028-5529 | 1 | 0.2599 | −14.17 | 355.39999 | 0 | 4 | 36.439999 |
| Y032-4567 | 1 | 0.2174 | −14.16 | 352.39999 | 0 | 4 | 40.619999 |
| S610-0136 | 1 | 0.3171 | −14.16 | 334.39999 | 0 | 4 | 40.619999 |
| S610-0028 | 1 | 0.2436 | −14.14 | 352.39999 | 0 | 4 | 40.619999 |
| 8008-4983 | 1 | 0.1208 | −14.12 | 396.5 | 0 | 4 | 40.619999 |
| F352-1296 | 1 | 0.1325 | −14.11 | 391.89999 | 1 | 4 | 37.27 |
| Y043-8161 | 1 | 0.1409 | −14.1 | 356.39999 | 1 | 3 | 54.369999 |
| T500-0491 | 1 | 0.1328 | −14.07 | 382.5 | 0 | 4 | 42.43 |
| S610-0034 | 1 | 0.1623 | −14.04 | 356.39999 | 0 | 4 | 40.619999 |
| M715-0199 | 0.99989998 | 0.1554 | −14.03 | 349.5 | 0 | 4 | 36.439999 |
| G658-0057 | 1 | 0.4719 | −14.02 | 299.39999 | 1 | 4 | 45.23 |
| M715-0628 | 1 | 0.2174 | −13.98 | 367.5 | 0 | 4 | 36.439999 |
| 2262-4096 | 1 | 0.4258 | −13.97 | 275.29999 | 1 | 4 | 54.349998 |
| SB76-0325 | 1 | 0.1847 | −13.96 | 366.39999 | 0 | 4 | 40.619999 |
| 8360-0211 | 1 | 0.2187 | −13.94 | 314.29999 | 1 | 4 | 59.060001 |
| Y030-3261 | 1 | 0.1815 | −13.94 | 316.39999 | 1 | 4 | 51.220001 |
| J042-0706 | 1 | 0.09976 | −13.93 | 374.39999 | 1 | 4 | 49.41 |
| G792-0616 | 1 | 0.2753 | −13.93 | 354.39999 | 0 | 4 | 40.619999 |
| G792-1812 | 1 | 0.1298 | −13.9 | 358.39999 | 1 | 4 | 49.41 |
| J042-0460 | 1 | 0.1782 | −13.89 | 382.89999 | 0 | 4 | 40.619999 |
| S509-2048 | 1 | 0.2001 | −13.89 | 360.5 | 0 | 4 | 40.619999 |
| M715-0157 | 0.99989998 | 0.1554 | −13.89 | 349.5 | 0 | 4 | 36.439999 |
| M715-0609 | 1 | 0.138 | −13.89 | 381.5 | 0 | 4 | 36.439999 |
| S690-1113 | 1 | 0.1428 | −13.88 | 390.5 | 0 | 4 | 40.619999 |
| SC09-0592 | 0.99919999 | 0.1547 | −13.87 | 308.39999 | 0 | 3 | 25.360001 |
| M715-0156 | 1 | 0.2654 | −13.87 | 335.39999 | 0 | 4 | 36.439999 |
| M715-0627 | 1 | 0.2387 | −13.87 | 353.5 | 0 | 4 | 36.439999 |
| M715-0625 | 1 | 0.171 | −13.86 | 381.5 | 0 | 4 | 36.439999 |
| SC09-0521 | 1 | 0.2944 | −13.85 | 334.39999 | 0 | 4 | 42.43 |
| L657-0028 | 1 | 0.1046 | −13.85 | 383.89999 | 0 | 4 | 36.439999 |
| J042-0257 | 1 | 0.1922 | −13.84 | 362.5 | 0 | 4 | 40.619999 |
| J042-0256 | 1 | 0.2374 | −13.82 | 348.39999 | 0 | 4 | 40.619999 |
| F344-1038 | 1 | 0.3093 | −13.81 | 334.79999 | 0 | 4 | 40.619999 |
| G658-0397 | 1 | 0.3464 | −13.79 | 313.39999 | 1 | 4 | 45.23 |
| M670-0146 | 0.99900001 | 0.1116 | −13.79 | 345.39999 | 0 | 4 | 38.130001 |
| 3381-0405 | 1 | 0.218 | −13.78 | 331.39999 | 0 | 4 | 36.439999 |
| T762-0711 | 1 | 0.1827 | −13.78 | 310.39999 | 1 | 4 | 44.810001 |
| SB66-0198 | 1 | 0.2187 | −13.78 | 353.39999 | 0 | 4 | 36.439999 |
| V020-4337 | 0.99989998 | 0.1256 | −13.78 | 385.5 | 0 | 4 | 36.439999 |
| G792-2259 | 0.99959999 | 0.1061 | −13.77 | 370.89999 | 1 | 4 | 49.41 |
| S994-0439 | 1 | 0.1137 | −13.76 | 413.5 | 0 | 5 | 43.860001 |
| S610-0043 | 1 | 0.1905 | −13.76 | 386.79999 | 0 | 4 | 40.619999 |
| S647-0245 | 1 | 0.2572 | −13.76 | 349.5 | 0 | 4 | 36.439999 |
| G792-2406 | 0.99989998 | 0.0998 | −13.75 | 368.39999 | 1 | 4 | 49.41 |
| V031-0643 | 1 | 0.2993 | −13.74 | 323.79999 | 1 | 4 | 54.880001 |
| Y031-5749 | 1 | 0.1544 | −13.74 | 382.5 | 0 | 4 | 40.619999 |
| G119-0015 | 1 | 0.3956 | −13.74 | 279.29999 | 2 | 4 | 57.779999 |
| SB76-0364 | 0.99989998 | 0.1598 | −13.74 | 362.5 | 0 | 4 | 40.619999 |
| 7491-0197 | 0.99949998 | 0.1055 | −13.74 | 314.39999 | 1 | 4 | 42.740002 |
| S513-0584 | 1 | 0.1031 | −13.73 | 449.5 | 0 | 7 | 62.32 |
| Y031-5404 | 1 | 0.2461 | −13.72 | 348.39999 | 0 | 4 | 40.619999 |
| G119-0253 | 0.99919999 | 0.1331 | −13.72 | 333.39999 | 1 | 4 | 39.34 |
| E822-2078 | 0.99989998 | 0.2256 | −13.72 | 311.79999 | 2 | 4 | 57.779999 |
| L609-0153 | 0.99959999 | 0.1062 | −13.71 | 351.39999 | 0 | 4 | 37.610001 |
| F352-0548 | 0.99989998 | 0.1074 | −13.71 | 403.5 | 1 | 4 | 37.27 |
| P114-0069 | 1 | 0.1791 | −13.7 | 351.79999 | 0 | 4 | 38.130001 |
| S610-0059 | 1 | 0.2522 | −13.7 | 368.89999 | 0 | 4 | 40.619999 |
| Y031-5630 | 1 | 0.1633 | −13.69 | 382.5 | 0 | 4 | 40.619999 |
| 7775-0011 | 1 | 0.2196 | −13.69 | 292.29999 | 2 | 4 | 56.330002 |
| S610-0018 | 1 | 0.2861 | −13.68 | 334.39999 | 0 | 4 | 40.619999 |
| S646-0205 | 0.99989998 | 0.1348 | −13.67 | 404.5 | 0 | 4 | 32.779999 |
| P114-0107 | 1 | 0.2066 | −13.67 | 349.39999 | 0 | 4 | 38.130001 |
| S610-0031 | 1 | 0.2349 | −13.67 | 348.39999 | 0 | 4 | 40.619999 |

TABLE 1-continued 100 potential CaMK2γ inhibitors

| ID | Lipinski Rule_Score | CNS Score | Docking Score | MW | HBD | HBA | TPSA |
|---|---|---|---|---|---|---|---|
| T500-0752 | 1 | 0.1567 | −13.66 | 368.39999 | 0 | 4 | 42.43 |
| 3574-0079 | 0.9982 | 0.139 | −13.66 | 378.29999 | 1 | 4 | 35.580002 |
| F234-0088 | 1 | 0.2163 | −13.66 | 345.39999 | 0 | 4 | 38.130001 |
| 3381-0411 | 0.99989998 | 0.1152 | −13.65 | 378.39999 | 0 | 4 | 32.779999 |
| T408-1594 | 1 | 0.1503 | −13.64 | 360.5 | 0 | 4 | 40.619999 |
| S512-0475 | 1 | 0.3274 | −13.64 | 308.39999 | 0 | 4 | 42.43 |
| 7999-0511 | 0.99720001 | 0.1046 | −13.63 | 368.20001 | 2 | 4 | 57.779999 |
| D391-0851 | 0.97960001 | 0.1278 | −13.62 | 320.39999 | 1 | 3 | 36.099998 |
| 7999-0509 | 0.99860001 | 0.1086 | −13.6 | 323.79999 | 2 | 4 | 57.779999 |
| D715-1709 | 1 | 0.1681 | −13.58 | 337.29999 | 1 | 4 | 54.880001 |
| E822-2401 | 0.97039998 | 0.1096 | −13.57 | 345.39999 | 2 | 4 | 57.779999 |
| Y031-5247 | 1 | 0.1685 | −13.57 | 356.39999 | 1 | 4 | 49.41 |
| 8016-8593 | 1 | 0.1823 | −13.57 | 307.29999 | 2 | 4 | 57.779999 |
| S329-0082 | 1 | 0.2197 | −13.57 | 366.5 | 0 | 5 | 41.490002 |
| G856-7286 | 1 | 0.244 | −13.55 | 306.39999 | 1 | 4 | 49.41 |
| Y040-9972 | 1 | 0.3227 | −13.55 | 299.79999 | 1 | 4 | 46.919998 |
| L423-0990 | 0.99980003 | 0.1406 | −13.54 | 364.5 | 1 | 4 | 49.41 |
| 8010-5836 | 0.99989998 | 0.2741 | −13.54 | 290.29999 | 0 | 4 | 51.549999 |
| 4964-2544 | 0.99900001 | 0.1439 | −13.52 | 362.39999 | 0 | 3 | 23.549999 |
| L413-0082 | 1 | 0.1306 | −13.51 | 405.5 | 0 | 5 | 43.860001 |
| S751-0758 | 0.99970001 | 0.2238 | −13.51 | 319.39999 | 1 | 4 | 46.919998 |

Then, 30 compounds are selected from the TargetMol database as potential CaMK2γ inhibitors, as shown in Table 2.

TABLE 2

30 potential CaMK2γ inhibitors

| ID | Lipinski Rule_Score | CNS Score | Docking Score | MW | HBD | HBA | TPSA |
|---|---|---|---|---|---|---|---|
| STOCKIN-74327 | 0.9988 | 0.05787 | −14.61 | 363.39999 | 3 | 4 | 60.68 |
| STOCKIN-93358 | 1 | 0.2258 | −13.54 | 308.39999 | 2 | 4 | 52.57 |
| T1187 | 0.8507 | 0.03872 | −13.31 | 310.39999 | 0 | 2 | 17.82 |
| TCD-N1050131 | 1 | 0.2258 | −13.04 | 308.39999 | 2 | 4 | 52.57 |
| TNP-005954 | 1 | 0.2515 | −12.63 | 307.39999 | 0 | 4 | 37.610001 |
| TNP-005666 | 1 | 0.1909 | −12.57 | 378.5 | 0 | 4 | 32.779999 |
| AE-562/43462260 | 1 | 0.1818 | −12.52 | 383.5 | 0 | 5 | 59 |
| TNP-006888 | 0.9965 | 0.1071 | −12.47 | 324.39999 | 0 | 3 | 36.259998 |
| T0459 | 1 | 0.1409 | −12.43 | 356.39999 | 1 | 3 | 54.369999 |
| TNP-005340 | 1 | 0.2625 | −12.42 | 254.3 | 2 | 3 | 39.259998 |
| T6493 | 0.9965 | 0.1071 | −12.4 | 324.39999 | 0 | 3 | 36.259998 |
| STOCKIN-07825 | 1 | 0.2258 | −12.38 | 308.39999 | 2 | 4 | 52.57 |
| TBB-03370 | 0.9997 | 0.1219 | −12.35 | 322.39999 | 2 | 4 | 58.919998 |
| NP-003263 | 1 | 0.2421 | −12.32 | 242.3 | 1 | 3 | 45.75 |
| T0862 | 0.9986 | 0.1498 | −12.19 | 309.39999 | 1 | 2 | 23.469999 |
| T0172 | 0.6794 | 0.1092 | −12.18 | 277.39999 | 1 | 1 | 12.03 |
| TBB-02910 | 1 | 0.4466 | −12.17 | 275.29999 | 0 | 4 | 38.77 |
| T1497 | 0.9999 | 0.2426 | −12.15 | 328.39999 | 0 | 4 | 34.59 |
| TNP-007710 | 0.9999 | 0.2426 | −12.14 | 328.39999 | 0 | 4 | 34.59 |
| N105-0131 | 1 | 0.2258 | −12.14 | 308.39999 | 2 | 4 | 52.57 |
| TSP-43462249 | 0.9998 | 0.1396 | −12.13 | 345.39999 | 1 | 3 | 30.49 |
| TNP-005964 | 1 | 0.2072 | −12.09 | 302.20001 | 1 | 4 | 54.860001 |
| N039-0003 | 1 | 0.251 | −12.07 | 292.39999 | 1 | 3 | 32.34 |
| T7085 | 0.9985 | 0.1891 | −12.06 | 276.39999 | 0 | 2 | 8.1700001 |
| T0113 | 0.9985 | 0.1891 | −12.06 | 276.39999 | 0 | 2 | 8.1700001 |
| NP-015687 | 1 | 0.1531 | −12.06 | 308.29999 | 2 | 4 | 66.760002 |
| T1509 | 0.9421 | 0.126 | −12.02 | 275.39999 | 0 | 1 | 3.24 |
| STOCKIN-28340 | 0.9993 | 0.1541 | −12.01 | 359.5 | 0 | 5 | 48 |
| TSP-43462257 | 1 | 0.2479 | −11.97 | 377.5 | 0 | 4 | 38.77 |
| T1275 | 1 | 0.2595 | −11.94 | 281.39999 | 2 | 4 | 47.860001 |

(5) Use of ADP-Go™ Kinase Assay+CaMK2γ Kinase Enzyme System (Promega #V9201) for Screening Compounds with Inhibitory Effect The kinase activity (%) of 130 compounds screened above are detected by ADP-Glo™ Kinase Assay+CaMK2γ Kinase Enzyme System (Promega #V9201), and the evaluation standard is kinase activity (%). Compared with the positive control (PC), a small molecule with the most significant inhibition effect (p<0.0001) is selected as a candidate ideal inhibitor, that is, the compound I (also referred to as T2533) used in the disclosure.

Figure 3A:
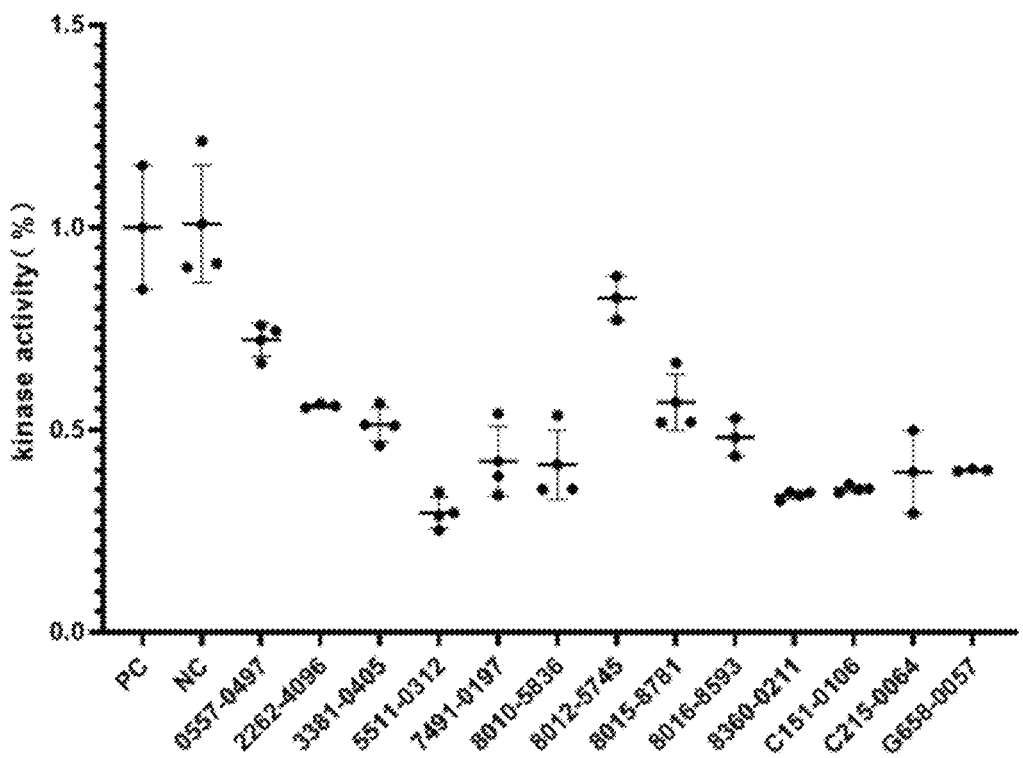
FIG. 3A illustrates a detection result a of preliminary screening for small molecule inhibitors of CaMK2γ by using adenosine diphosphate (ADP)-Glo™ Kinase Assay+CaMK2γ Kinase Enzyme System (Promega #TM313).
Figure 3B:
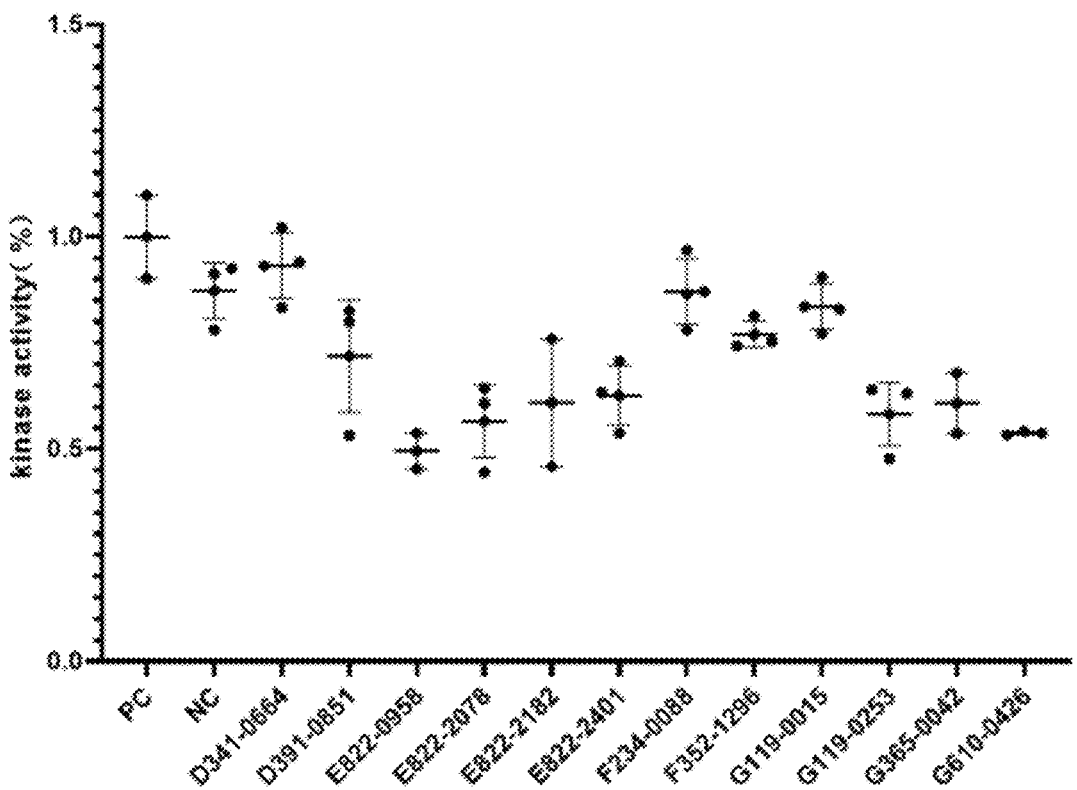
FIG. 3B illustrates a detection result b of preliminary screening for small molecule inhibitors of CaMK2γ by using ADP-Glo™ Kinase Assay+CaMK2γ Kinase Enzyme System (Promega #TM313).
Figure 3C:
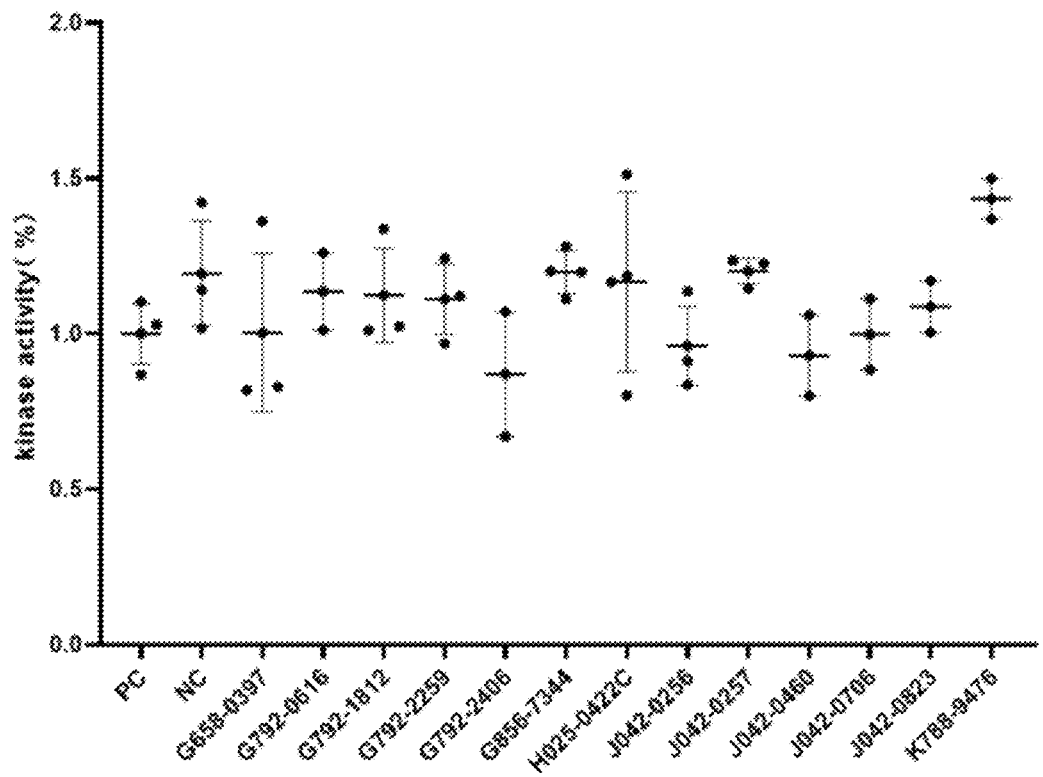
FIG. 3C illustrates a detection result c of preliminary screening for small molecule inhibitors of CaMK2γ by using ADP-Glo™ Kinase Assay+CaMK2γ Kinase Enzyme System (Promega #TM313).
Figure 3D:
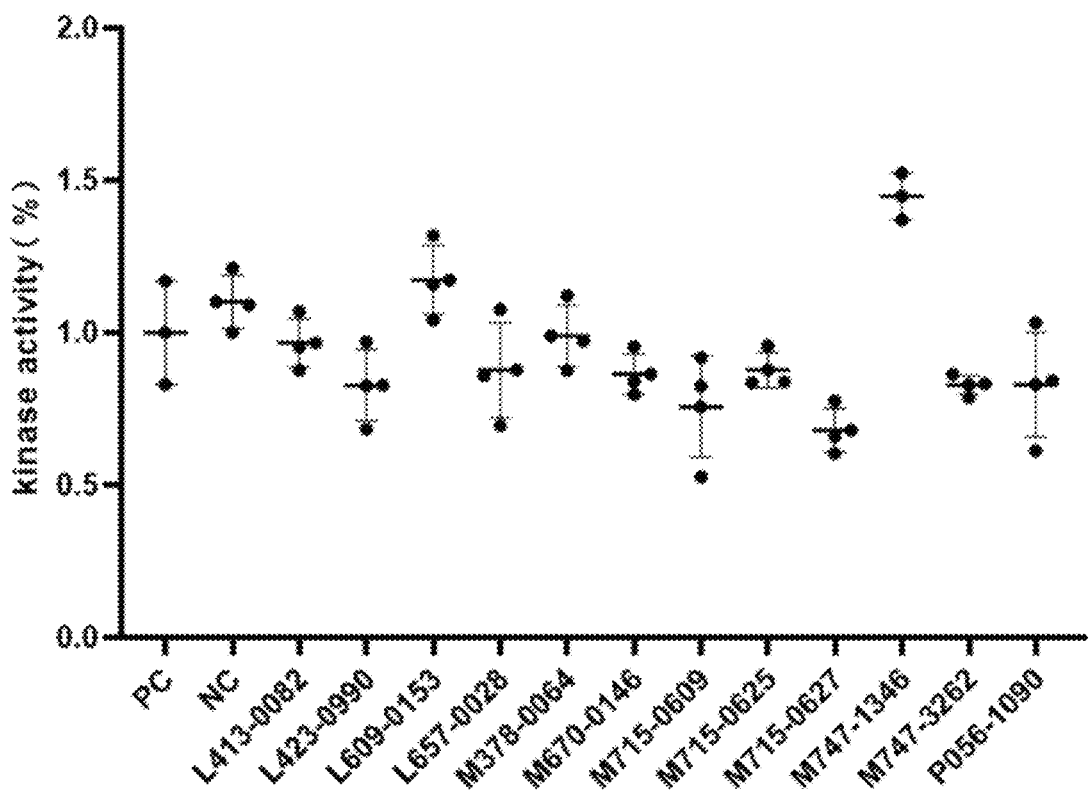
FIG. 3D illustrates a detection result d of preliminary screening for small molecule inhibitors of CaMK2γ by using ADP-Glo™ Kinase Assay+CaMK2γ Kinase Enzyme System (Promega #TM313).
Figure 3E:
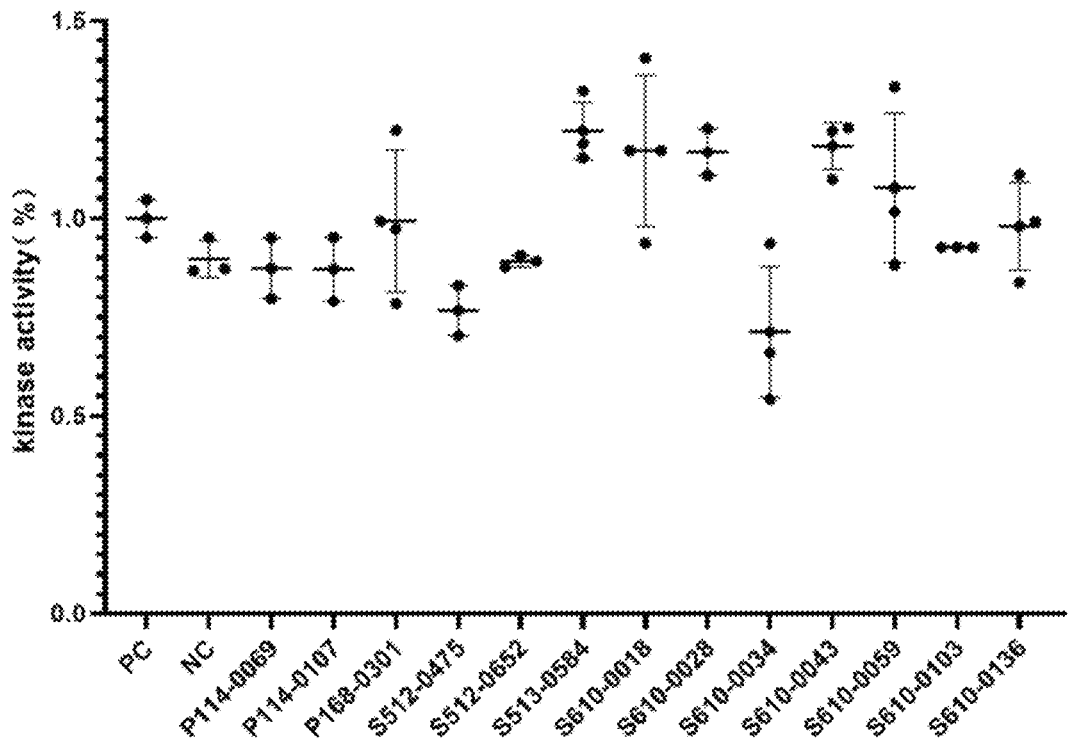
FIG. 3E illustrates a detection result e of preliminary screening for small molecule inhibitors of CaMK2γ by using ADP-Glo™ Kinase Assay+CaMK2γ Kinase Enzyme System (Promega #TM313).
Figure 3F:
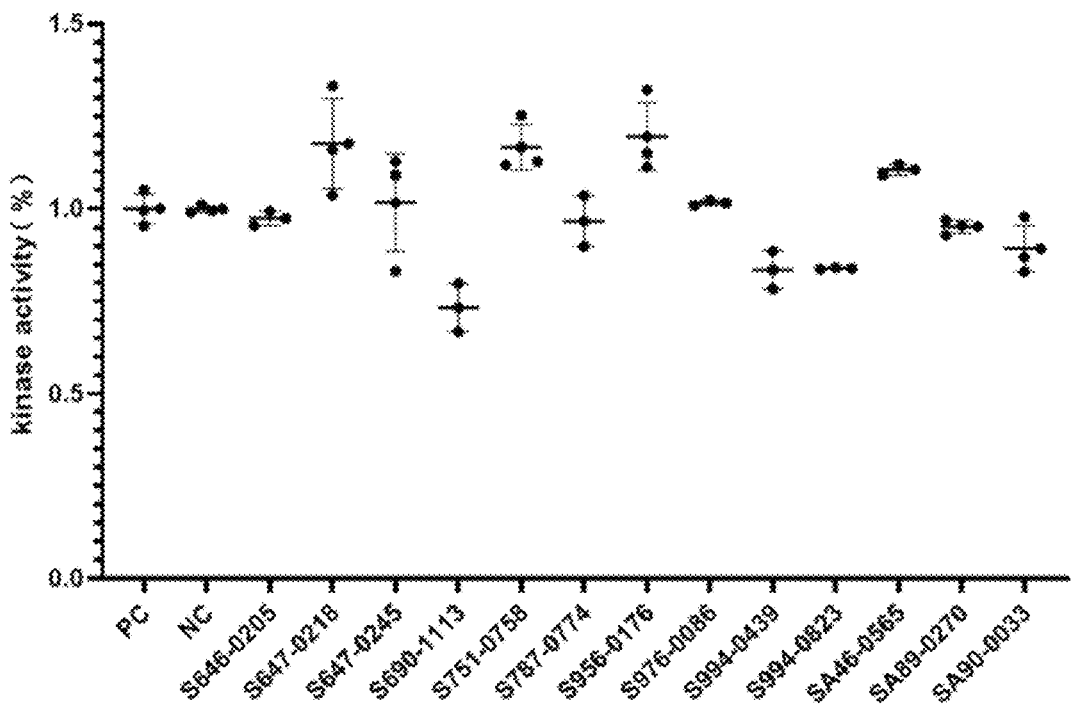
FIG. 3F illustrates a detection result f of preliminary screening for small molecule inhibitors of CaMK2γ by using ADP-Glo™ Kinase Assay+CaMK2γ Kinase Enzyme System (Promega #TM313).
Figure 3G:
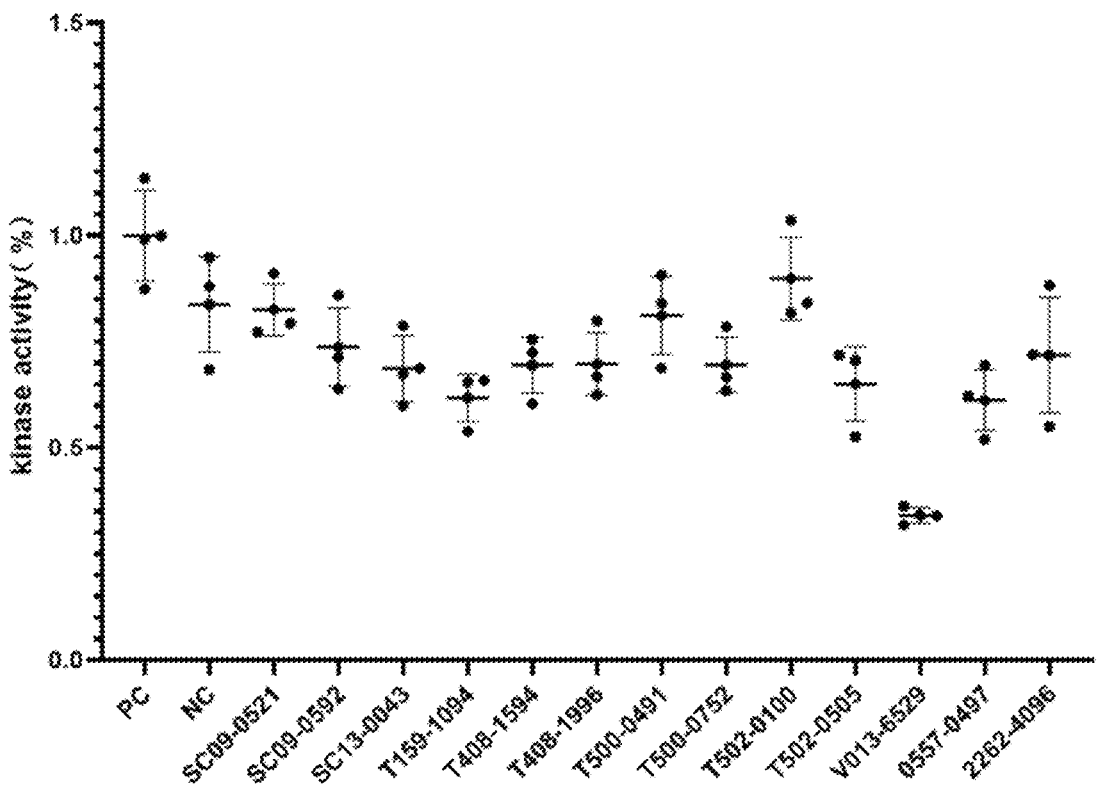
FIG. 3G illustrates a detection result g of preliminary screening for small molecule inhibitors of CaMK2γ by using ADP-Glo™ Kinase Assay+CaMK2γ Kinase Enzyme System (Promega #TM313).
Figure 3H:
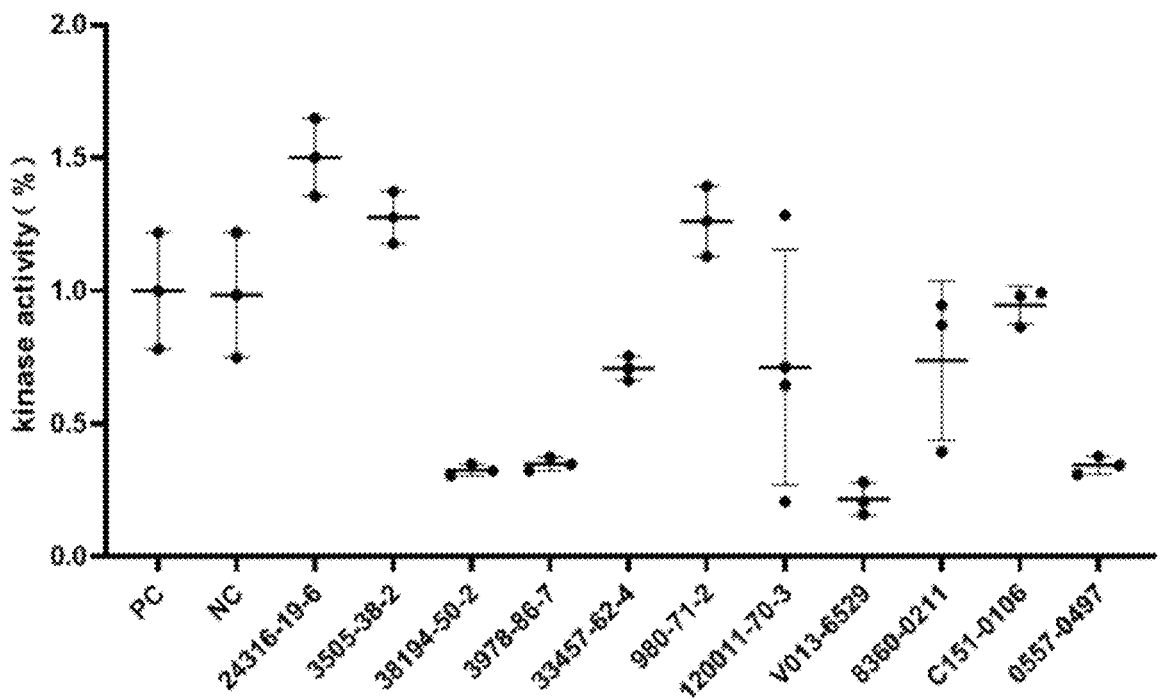
FIG. 3H illustrates a detection result h of preliminary screening for small molecule inhibitors of CaMK2γ by using ADP-Glo™ Kinase Assay+CaMK2γ Kinase Enzyme System (Promega #TM313).
Figure 3I:
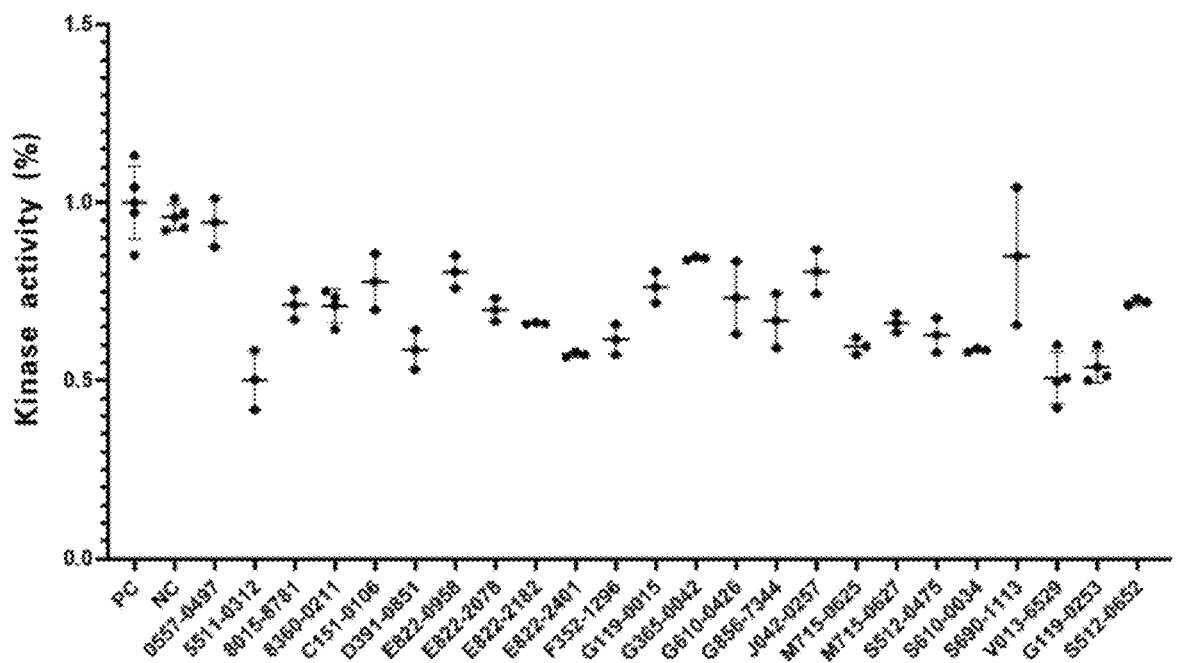
FIG. 3I illustrates a detection result i of preliminary screening for small molecule inhibitors of CaMK2γ by using ADP-Glo™ Kinase Assay+CaMK2γ Kinase Enzyme System (Promega #TM313).
Figure 3J:
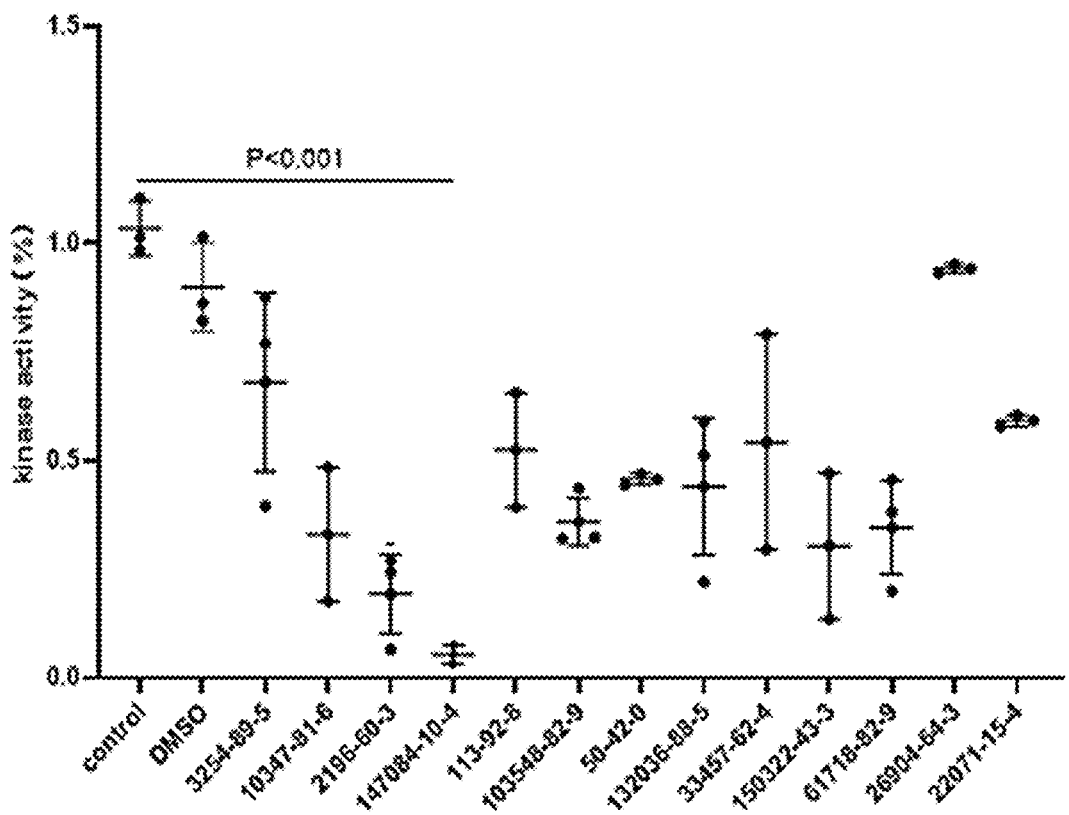
FIG. 3J illustrates a detection result j of preliminary screening for small molecule inhibitors of CaMK2γ by using ADP-Glo™ Kinase Assay+CaMK2γ Kinase Enzyme System (Promega #TM313).
Figure 3K:
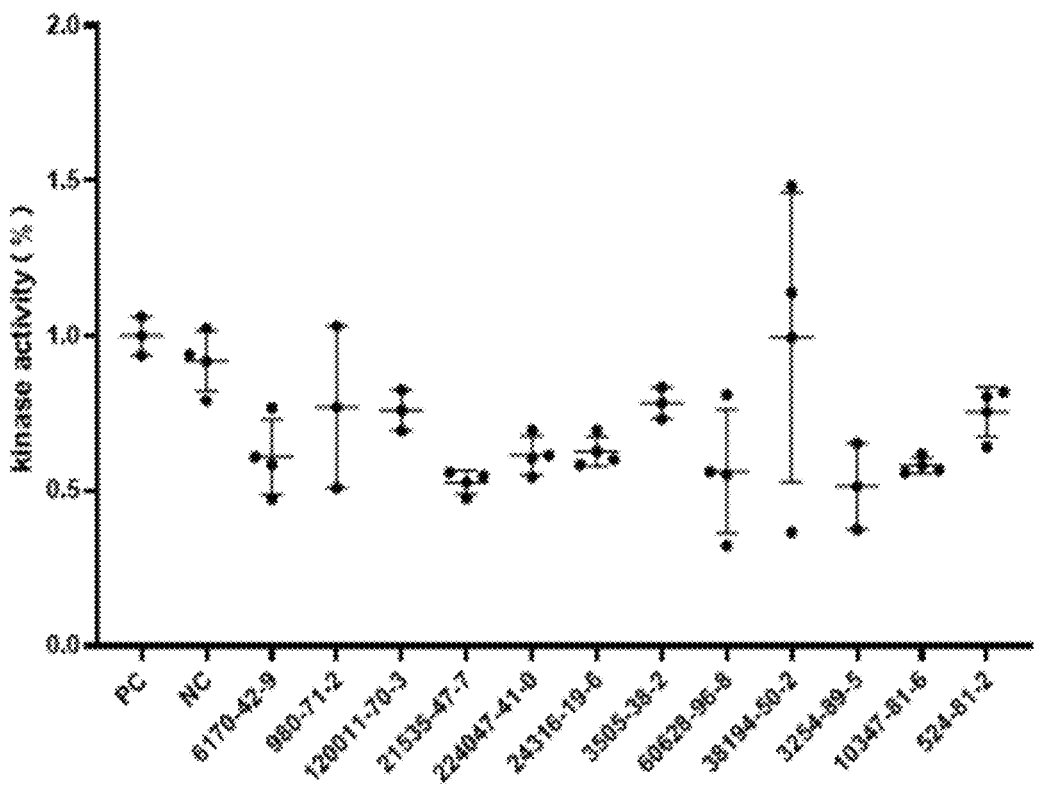
FIG. 3K illustrates a detection result k of preliminary screening for small molecule inhibitors of CaMK2γ by using ADP-Glo™ Kinase Assay+CaMK2γ Kinase Enzyme System (Promega #TM313).
Figure 3L:
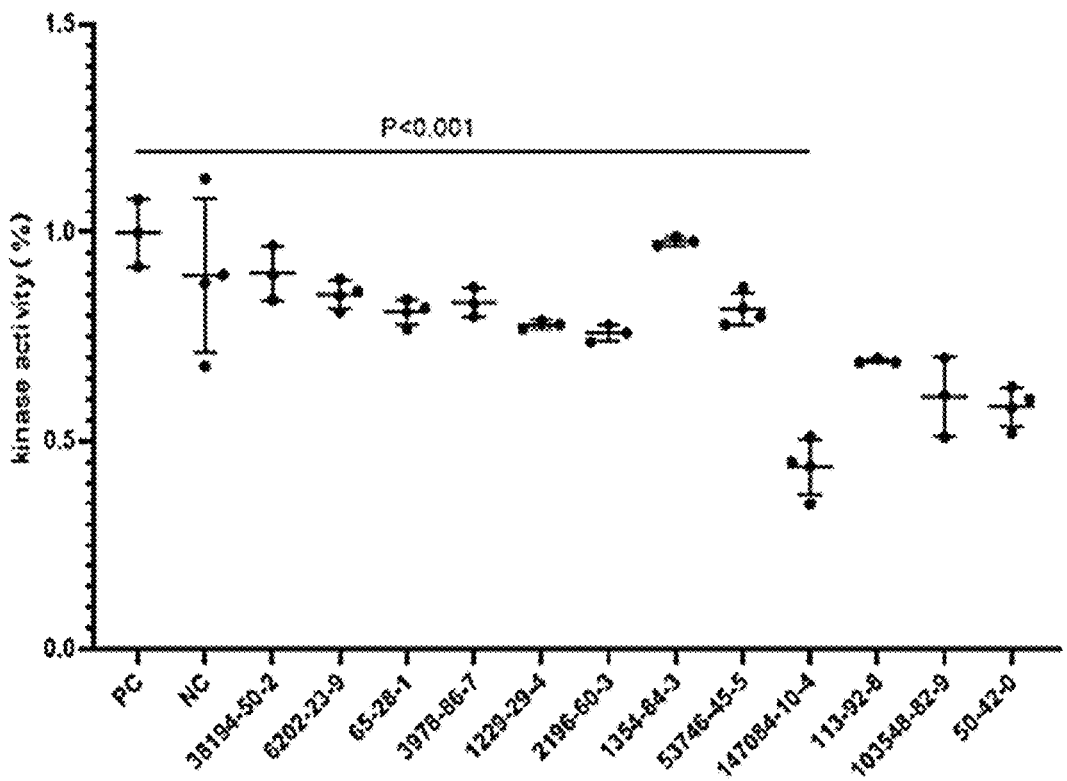
FIG. 3L illustrates a detection result l of preliminary screening for small molecule inhibitors of CaMK2γ by using ADP-Glo™ Kinase Assay+CaMK2γ Kinase Enzyme System (Promega #TM313).
Figure 3M:
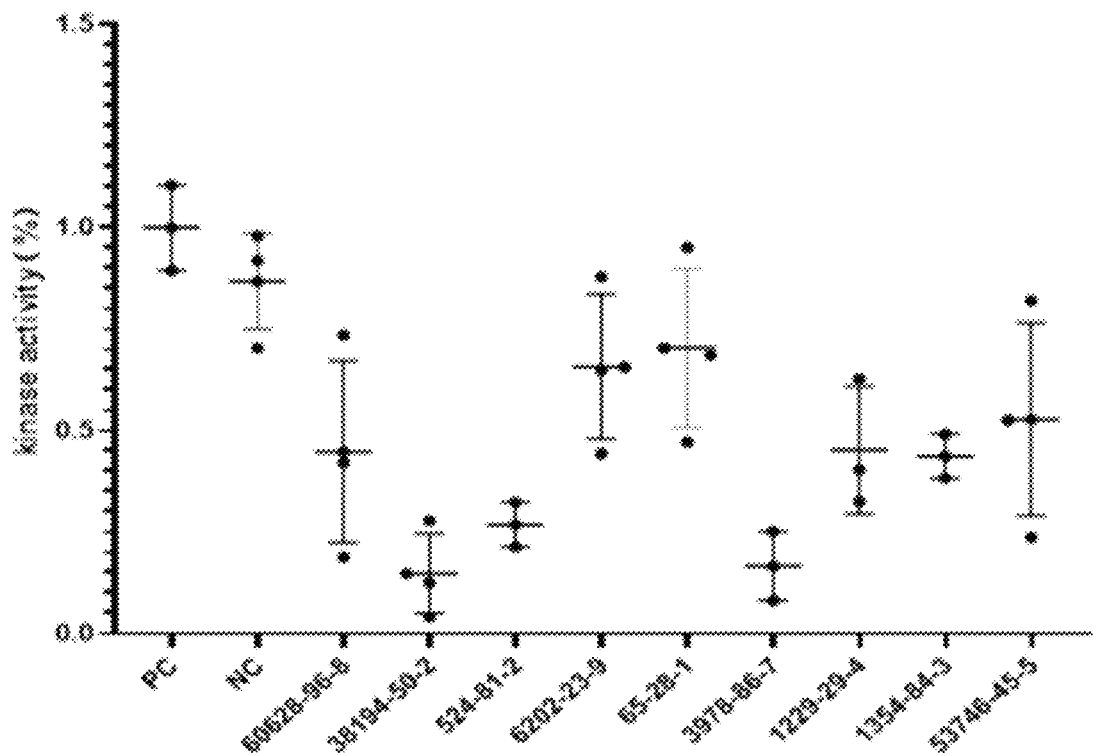
FIG. 3M illustrates a detection result m of preliminary screening for small molecule inhibitors of CaMK2γ by using ADP-Glo™ Kinase Assay+CaMK2γ Kinase Enzyme System (Promega #TM313).
Figure 3N:
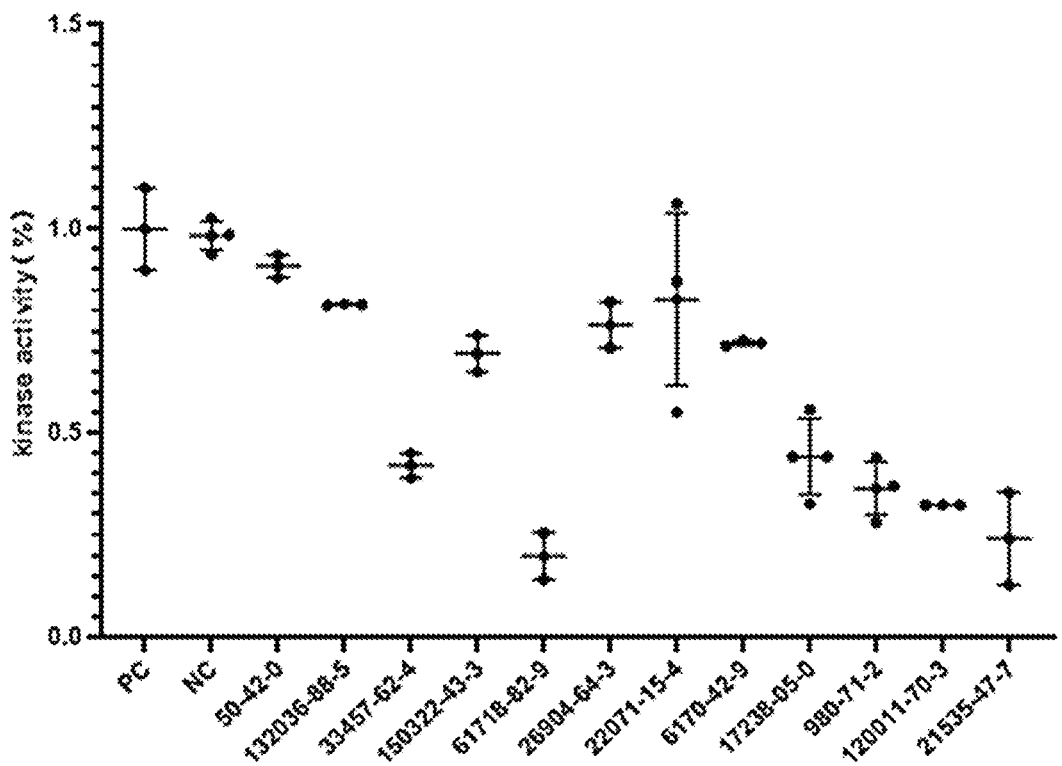
FIG. 3N illustrates a detection result n of preliminary screening for small molecule inhibitors of CaMK2γ by using ADP-Glo™ Kinase Assay+CaMK2γ Kinase Enzyme System (Promega #TM313).

The kinase activity (%) of each well is calculated by the above method. Among 130 small molecule inhibitors, the small molecule with the most significant inhibition effect (p<0.0001) is selected as a candidate ideal inhibitor. The results are shown in FIG. 3A-FIG. 3N.

The small molecule compound I screened in the above method is Alcaftadine, with a molecular weight of 307.39, and a structural formula the compound I is shown in a formula I expressed as follows:

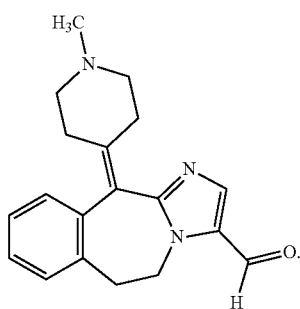

formula I

The small molecule compound I selected above is characterized step (1) and step (2) as follows.

Figure 4:
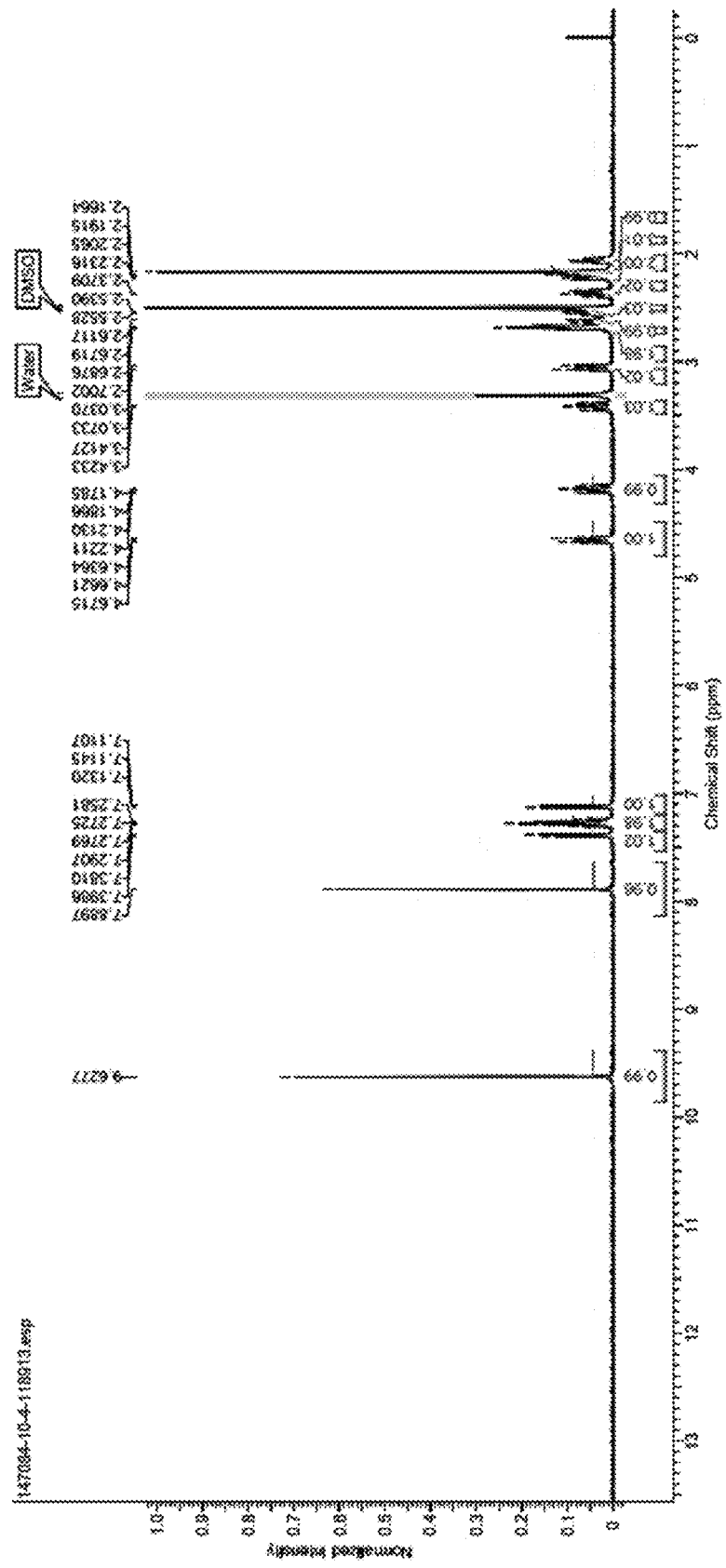
FIG. 4 illustrates a nuclear magnetic resonance (NMR) spectrum of T2533.

Step (1), the small molecule compound I is characterized by nuclear magnetic resonance (NMR) spectrum, results are shown in FIG. 4, which is consistent with the structure of the compound, and the structure of the compound is correct.

Figure 5:
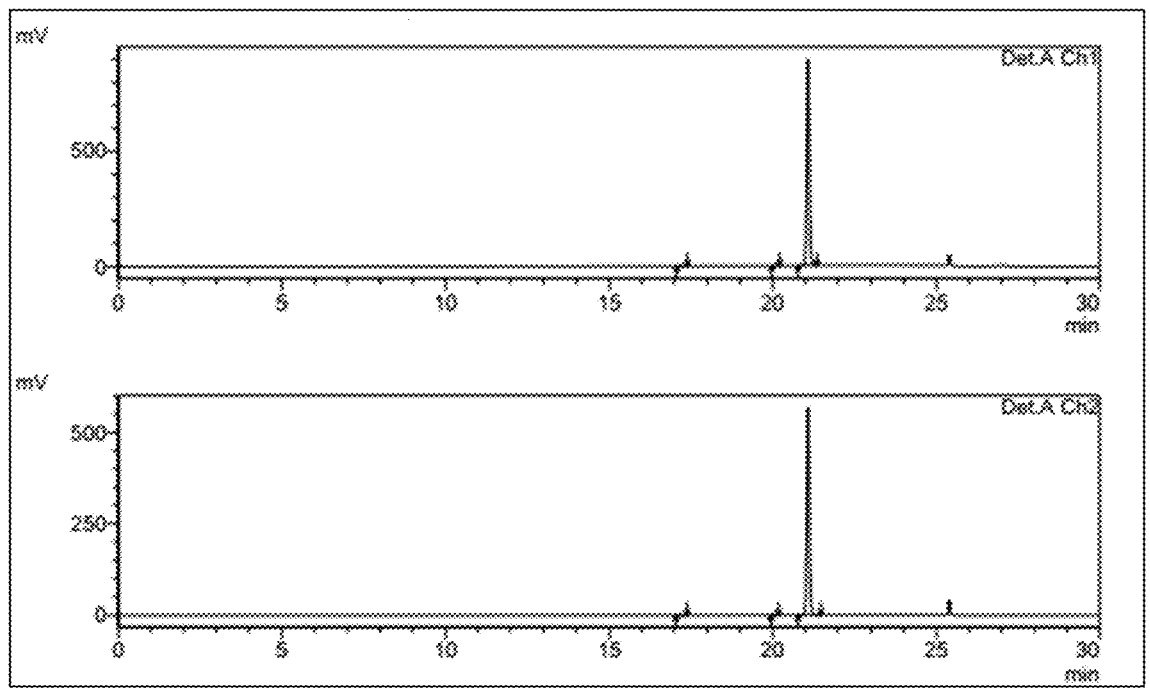
FIG. 5 illustrates a high-performance liquid chromatography (HPLC) chromatogram of T2533.

Step (2), the small molecule compound I is detected by high-performance liquid chromatography (HPLC), and results are shown in FIG. 5 and Table 3 (254 nanometers abbreviated nm) and Table 4 (220 nm), which are consistent with the characteristics of the target compound.

TABLE 3

Results detected by HPLC at 254 nm of a wavelength detector

| Peak# | Ret. Time | Area | Area % | Theoretical Plate |
|---|---|---|---|---|
| 1 | 17.195 | 1531 | 0.048 | 119464.370 |
| 2 | 20.066 | 2719 | 0.085 | 255695.238 |
| 3 | 21.084 | 3187328 | 99.867 | 275249.218 |
|  |  | 3191577 | 100.00 |  |

TABLE 4

Results detected by HPLC at 220 nm of a wavelength detector

| Peak# | Ret. Time | Area | Area % | Theoretical Plate |
|---|---|---|---|---|
| 1 | 17.198 | 2249 | 0.044 | 140932.879 |
| 2 | 20.066 | 4395 | 0.087 | 284614.153 |
| 3 | 21.084 | 5058660 | 99.869 | 275412.689 |
|  |  | 5065304 | 100.00 |  |

The synthetic route of the above screened small molecular compound I is as follows:

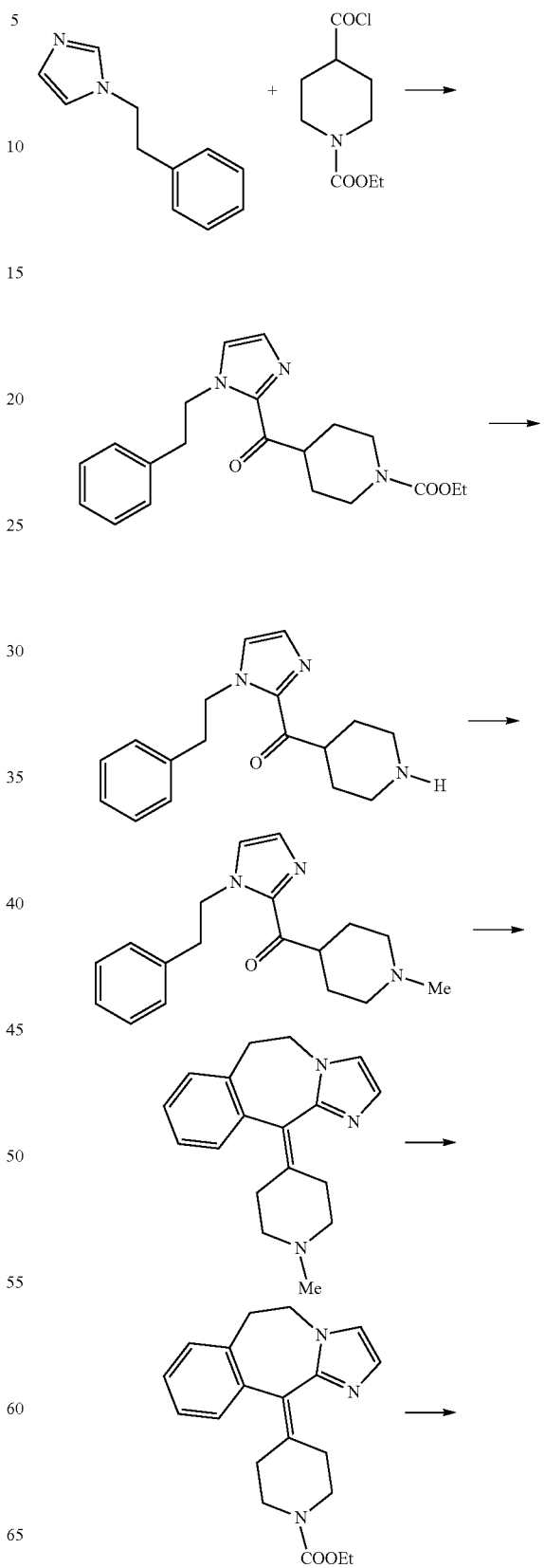

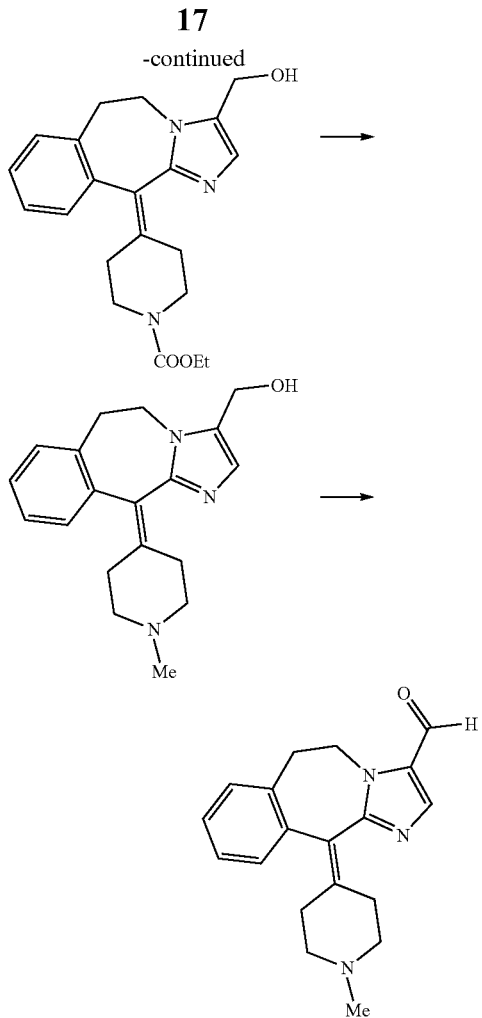

In the following embodiments, the statistical analysis of data is performed using SPSS 23.0 and RVersion 4.0.2 software to process and analyze data. All tests are two-sided test, and a P value of less than 0.05 is considered statistically significant.

In order to better understand the disclosure, the content of the disclosure is further illustrated below in combination with specific embodiments, but the content of the disclosure is not limited to the following embodiments.

Embodiment 1 an Interaction Pattern Between T2533 and CaMK2γ Protein

Figure 6A:
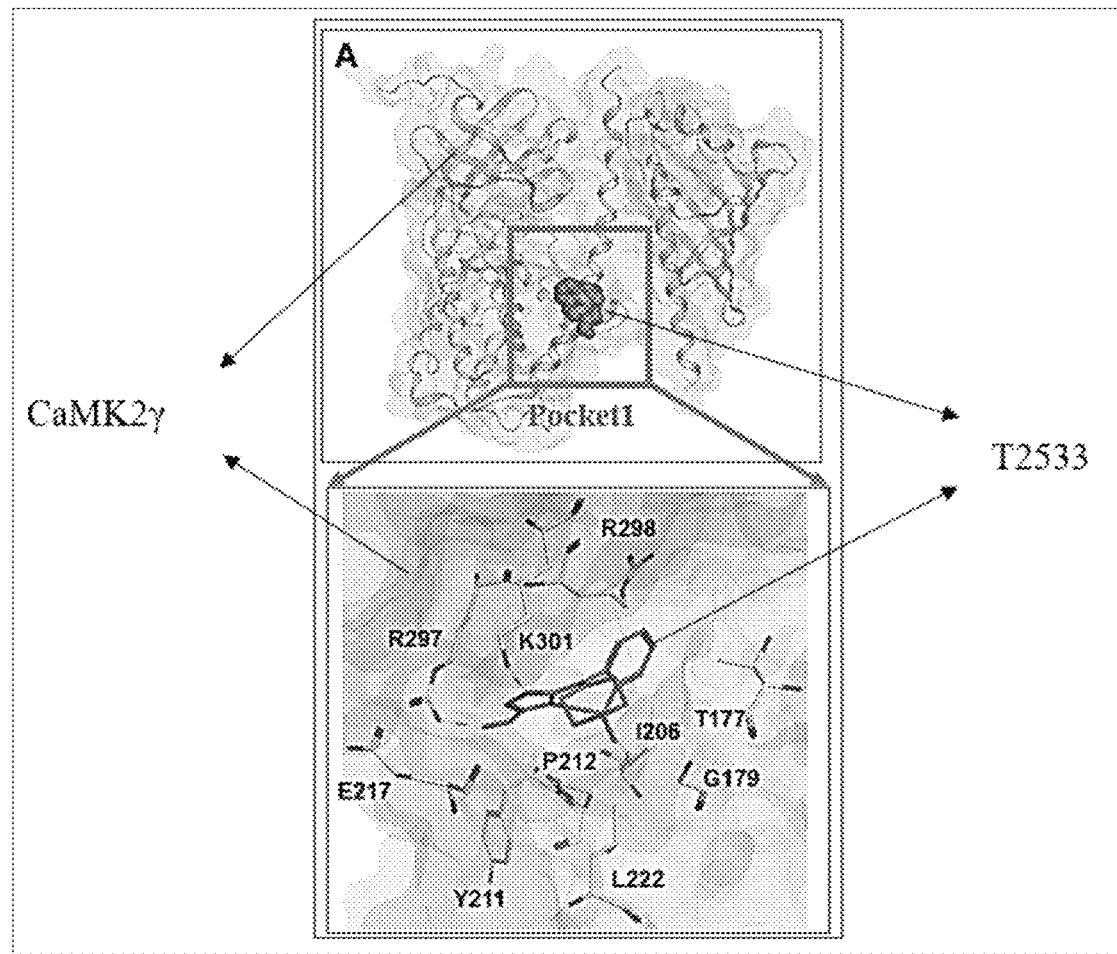
FIG. 6 illustrates an interaction pattern between T2533 and CaMK2γ protein.
Figure 6B:
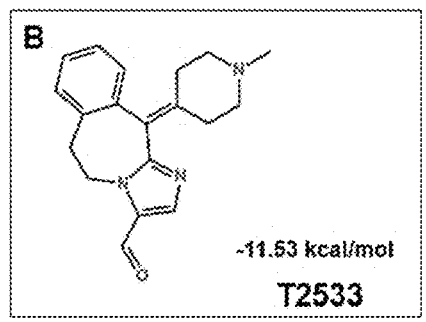
Figure 6C:
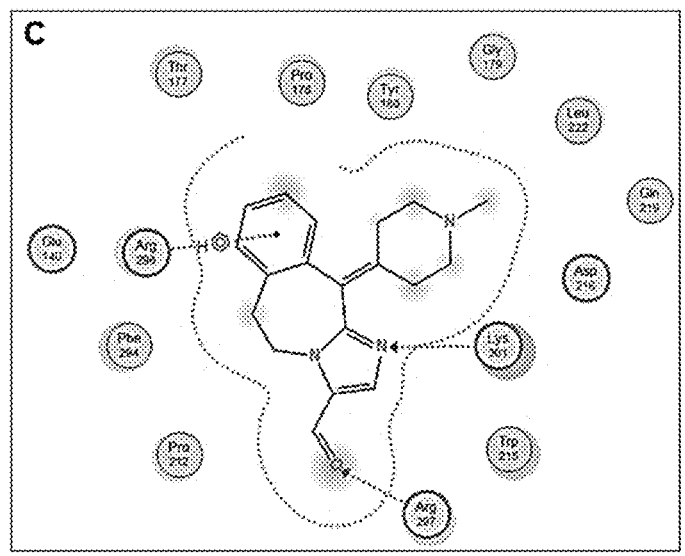

In the embodiment of the disclosure, the structure of T2533 is combined with CaMK2γ protein is simulated. Specifically, two rounds of combination simulation are firstly performed by using a Surflex module in Sybyl-X2.1 software, and then multiple hydrogen bond interactions are formed with multiple amino acids such as arginine 24 (Arg24), leucine 72 (Leu72), asparagine (Asn73) and other amino acids on the CaMK2γ for manual screening and review. As shown in FIGS. 6A-6C, T2533 has a strong hydrophobic interaction with multiple hydrophobic amino acids, such as Arg24 (a hydrophobic part of side chain), lysine 26 (abbreviated Lys26, a hydrophobic part of side chain), phenylalanine 27 (Phe27), Phe28, Leu40, histidine 41 (His41), Lys71 (a hydrophobic part of side chain) and Leu72. In addition, the compound T2533 forms a π-π stacking interaction with Phe27 and Phe28. It can be seen that the hydrophobic π-π stacking and other interactions jointly maintain the binding of compound T2533 to the CAMK2γ protein.

Figure 7:
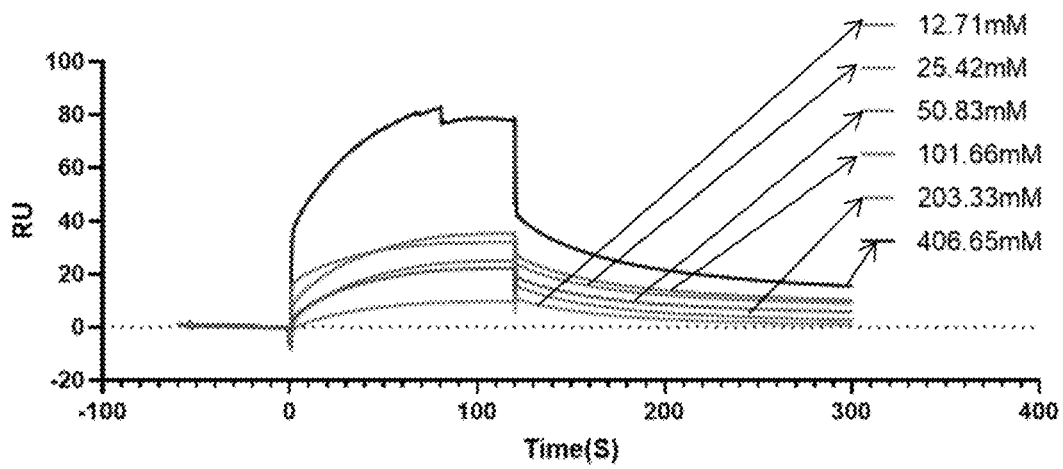
FIG. 7 illustrates a detection result of affinity between T2533 and human-derived CaMK2γ protein.

Embodiment 2 Detection for Strong Affinity Between T2533 and Human-Derived CaMK2γ Protein In the embodiment of the disclosure, the affinity between T2533 and human-derived CaMK2γ protein are detected. Specifically, a pET28A vector is firstly used to express and purify the human-derived full-length CaMK2γ protein. Subsequently, the affinity is determined by the surface plasmon resonance (SPR) method of Biacore™ using a CM5 chip amine-coupling. The detection results are shown in FIG. 7, and the results show that T2533 is specifically bound to the human-derived CaMK2γ protein, the binding constant is $2.54 \times 10^{-5}$ moles per liter (M), and has a strong combining ability.

Figure 8:
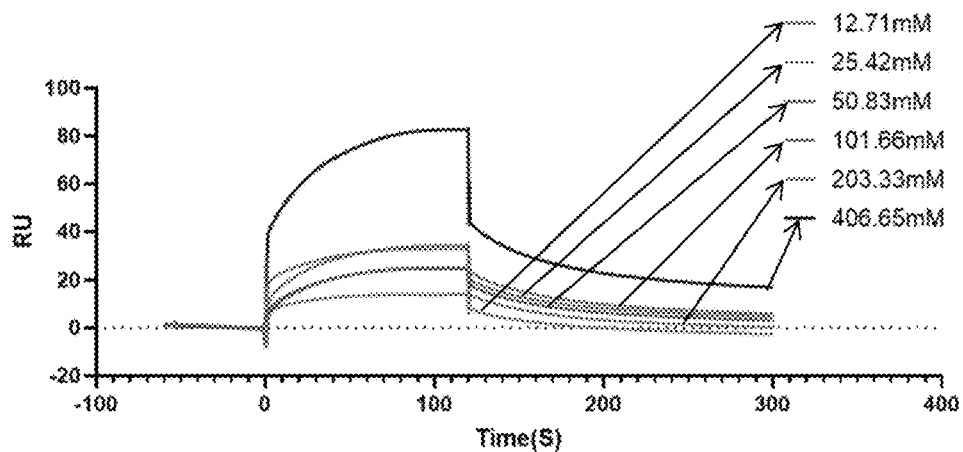
FIG. 8 illustrates a detection result of affinity between T2533 and mouse-derived CaMK2γ protein.
Figure 9:
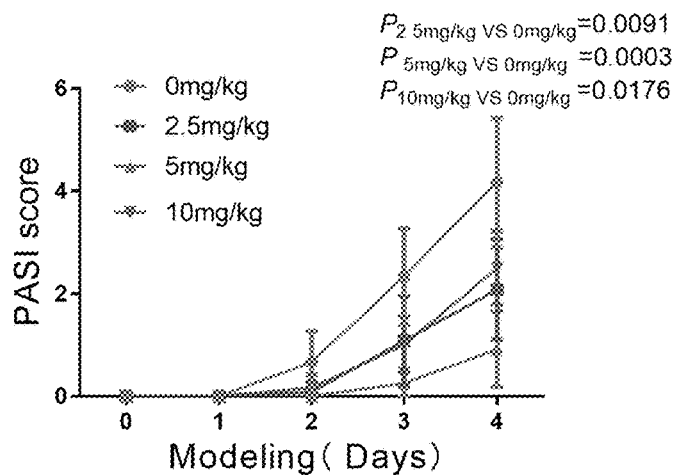
FIG. 9 illustrates Psoriasis Area and Severity Index (PASI) scores of mice of respective treatment groups.
Figure 10:
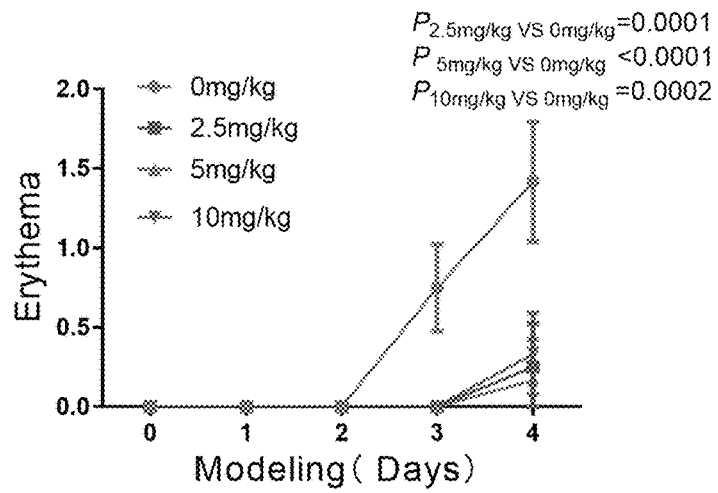
FIG. 10 illustrates statistics of degrees of erythema of mice of respective treatment groups.
Figure 11:
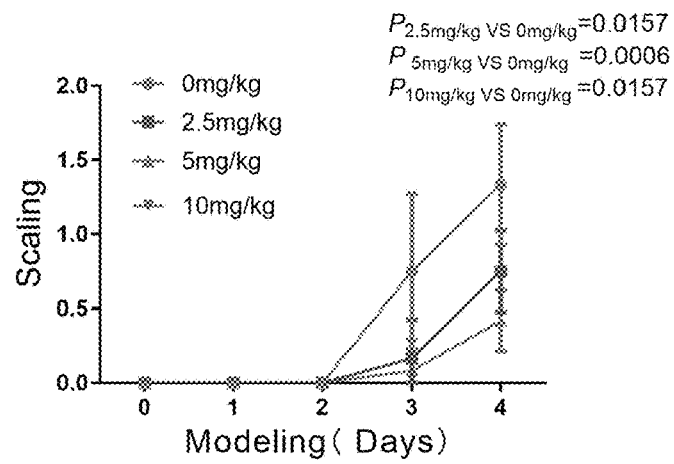
FIG. 11 illustrates statistics of degrees of scaling of mice of respective treatment groups.
Figure 12:
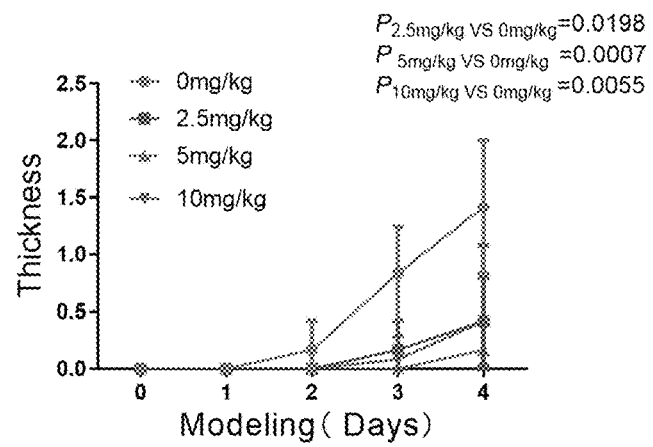
FIG. 12 illustrates statistics of skin thickness of mice of respective treatment groups.

Embodiment 3 Detection for Strong Affinity Between T2533 and Mouse-Derived CaMK2γ Protein In the embodiment of the disclosure, the affinity between T2533 and mouse-derived CaMK2γ protein are detected. Specifically, a pET28A vector is firstly used to express and purify the mouse-derived full-length CaMK2γ protein. Subsequently, the affinity is determined by the SPR method of Biacore™ using a CM5 chip amine-coupling. The detection results are shown in FIG. 8, and the results show that T2533 is specifically bound to the mouse-derived CaMK2γ protein, the binding constant is $6.84 \times 10^{-5}$ M, and has a strong combining ability.

Embodiment 4 Test of T2533 for Effectively Inhibiting CaMK2γ Protein Activity

In the embodiment of the disclosure, the inhibition of T2533 on CaMK2γ protein activity is detected by ADP-Glo™ Kinase Assay+CaMK2 γ Kinase Enzyme System (Promega #V9201), and the specific experimental steps and settings are as follows.

(1) well setting: 2 blank wells, 2 normal reaction wells, 2 dimethyl sulfoxide (DMSO) control wells, 40 inhibitor wells with 2 plex wells for each inhibitor and 20 inhibitors. There are 46 wells in total.

(2) preparation of a kinase reaction reagent:
(a) preparation of 200 microliters (L) 4× Kinase Buffer is as shown in Table 5 below. 175 μL of the 4× Kinase Buffer is required for a single experiment, that is, 2.5*20+62.5+62.5=175 μL. The rest is prepared into 1× Kinase Buffer and used as blank well.

TABLE 5

| Kinase Buffer reagent | |
| --- | --- |
| 5X Reaction Buffer A | 160 μL |
| Dithiothreitol (abbreviated DTT, 0.1 mole per liter abbreviated M) | 0.4 μL |
| Water | 39.6 μL |

(b) preparation of 10 μL 5× inhibitor solution (final concentration is 10 micromoles per liter abbreviated μM), and 2.5 μL/well. Specifically, the inhibitor is 10 millimoles per liter abbreviated mM, diluted to 1 mM with DMSO in a ratio of 1:9; the preparation method of DMSO is the same as that of inhibitor, which is used as the DMSO control well, as shown in Table 6 below.

TABLE 6

| Inhibitor Solution Reagent | |
| --- | --- |
| 4X Kinase Buffer | 2.5 μL |
| Inhibitor in DMSO (1 mM) | 0.5 μL |
| Water | 7 μL |

(c) preparation of 250 μL 2.5× adenosine triphosphate (ATP)/Autocamtide-2 (final concentration of 25 μM ATP and 0.2 μg/L of Autocamtide-2), and 5 μL/well. Specifically, ATP is 10 mM, diluted with water at 1:39 to 250 μM, Autocamtide-2 is divided into 270 μL per tube after the first thawing, available twice, as shown in Table 7 below.

TABLE 7

| ATP/Autocamtide-2 Reagent | |
| --- | --- |
| 4X Kinase Buffer | 62.5 μL |
| ATP (250 UM) | 62.5 μL |
| Autocamtide-2 (1 mg/mL) | 125 μL |

(d) preparation of 250 μL 2.5× CaMK2γ/Ca$^{2+}$/Calmodulin solution II (5 nanograms abbreviated ng CaMK2γ/12.5 μL), and 5 μL/well. Specifically, CaMK2γ is divided into 7 μL per tube after the first thawing, available twice, as shown in Table 8 below.

TABLE 8

| CaMK2γ/Ca$^{2+}$/Calmodulin solution II reagent | |
| --- | --- |
| 4X Kinase Buffer | 62.5 μL |
| CaMK2γKinase (100 ng/μL) | 2.5 μL |
| Ca$^{2+}$/Calmodulin solution II (10X) | 62.5 μL |
| Water | 122.5 μL |

(2) kinase reaction is carried out according to the following steps. (a) the reagents are added to reagent wells as follows: the blank well is added with 7.5 μL 1× Kinase Buffer; the normal reaction well is added with 2.5 μL 1× Kinase Buffer and 5 μL 2.5× CaMK2γ/Ca$^{2+}$/Calmodulin solution II; the DMSO control well is added with 2.5 μL 5×DMSO and 5 μL 2.5× CaMK2γ/Ca$^{2+}$/Calmodulin solution I; and the inhibitor well is added with 2.5 μL 5× inhibitor solution and 5 μL 2.5× CaMK2γ/Ca$^{2+}$/Calmodulin solution II. (b) the wells are blown and mixed evenly, and incubated at room temperature for 10 minutes. (c) each well is added with 5 μL 2.5×ATP/Autocamtide-2. (d) the wells are blown and mixed evenly, and incubated at room temperature for 60 minutes. (e) each well is added with 12.5 μL adenosine diphosphate (ADP)-Glo reagent for ADP-Glo reaction (the ADP-Glo reagent is divided into 2500 μL per tube after the first thawing, available twice). (f) the wells are blown and mixed evenly, and incubated at room temperature for 40 minutes. (g) each well is added with 25 μL kinase detection reagent (the kinase detection reagent is divided into 2500 μL per tube after the first thawing, available twice). (h) the wells are blown and mixed evenly, and incubated at room temperature for 30 minutes. (i) chemiluminescence detection is performed with Integration time 0.5-1 sec.

The compound (T2533) is found to effectively reduce the expression of CaMK2γ protein by analyzing and calculating the kinase activity (%) passing through each well after the relevant experimental operations are completed according to the above steps.

Embodiment 5 Test of T2533 for Effectively Inhibiting CaMK2γ Protein Activity in a Psoriatic Animal Model DMSO is used to dissolve T2533 powder, the T2533 powder is weighed according to different dosage, and then diluted with β-cyclodextrin, the final concentration of DMSO is not more than 5%. The dose gradient of T2533 is 0 mg/kg, 2.5 mg/kg, 5 mg/kg, and 10 mg/kg. Each mouse is calculated as 20 grams (g), and each mouse needs to be administered 0 mg, 0.05 mg, 0.1 mg, and 0.2 mg per day.

Seven-week-old C57/BL6 mice are bred and modeled in SPF-level environment. The experimental groups are as follows: (1) applying the skin with imiquimod (IMQ) and 0 mg/kg T2533; (2) applying the skin with IMQ and 2.5 mg/kg T2533; (3) applying the skin with IMQ and 5 mg/kg T2533; (4) applying the skin with IMQ and 10 mg/kg T2533; (5) applying the skin with Vaseline® and 0 mg/kg T2533; (6) applying the skin with Vaseline® and 2.5 mg/kg T2533; (7) applying the skin with Vaseline® and 5 mg/kg T2533; and (8) applying the skin with Vaseline® and 10 mg/kg T2533.

In each group of 6 mice, the hair on the back of the mice is shaved to make the exposed skin reach 4 square centimeters. The start date of the experiment is set as Day-2, and the end date is set as Day4. From Day-2 to Day3, 200 μL of liquid drug is taken in the morning and evening every day and evenly smeared on the skin of mice until it is absorbed. From Day 0 to Day 3, 62.5 mg IMQ is applied to each mouse at noon of every day. The skin of mice is scored every day, the mice are euthanized on Day 4, and the skin tissues are taken for a series of detection.

Figure 13:
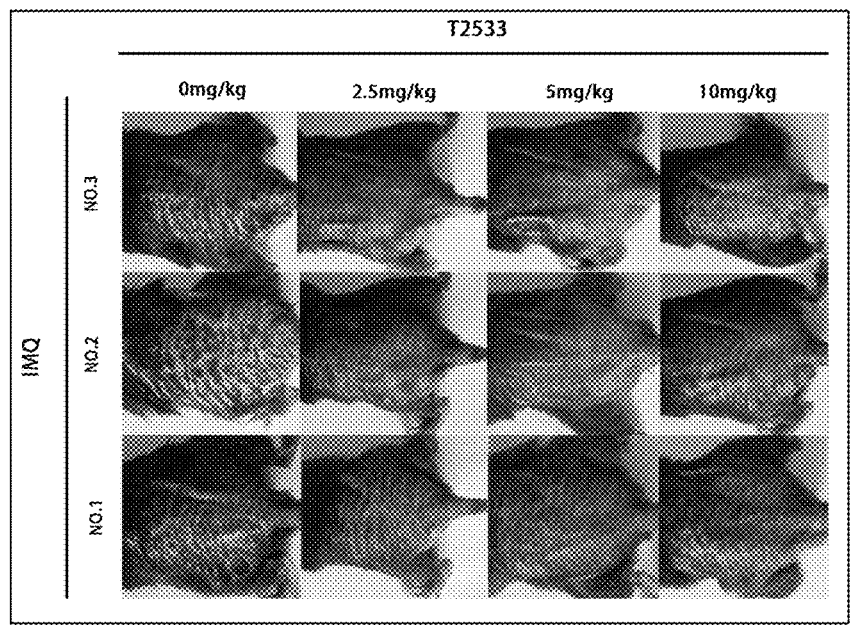
FIG. 13 illustrates phenotypes of imiquimod (IMQ)-induced after smeared with T2533 of respective treatment groups.
Figure 14:
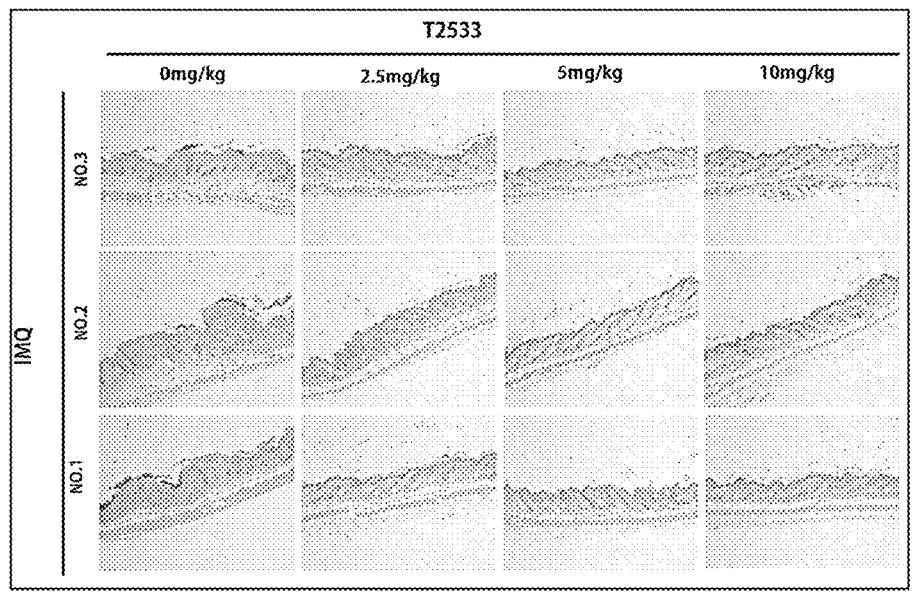
FIG. 14 illustrates skin pathological phenotypes of mice of respective treatment groups.

The PASI score results and the corresponding score results of erythema, scaling, and skin thickness of the above IMQ modelled mice are shown in FIG. 9, FIG. 10, FIG. 11, and FIG. 12, respectively. The skin phenotypes and skin pathological phenotypes are shown in FIG. 13 and FIG. 14, respectively. T2533 at 2.5 mg/kg, 5 mg/kg and 10 mg/kg reduces the inflammatory phenotype of IMQ-induced mice to varying degrees, of which 5 mg/kg is the most significant, followed by 2.5 mg/kg and 10 mg/kg, and the overall effect has no significant difference.

Figure 15:
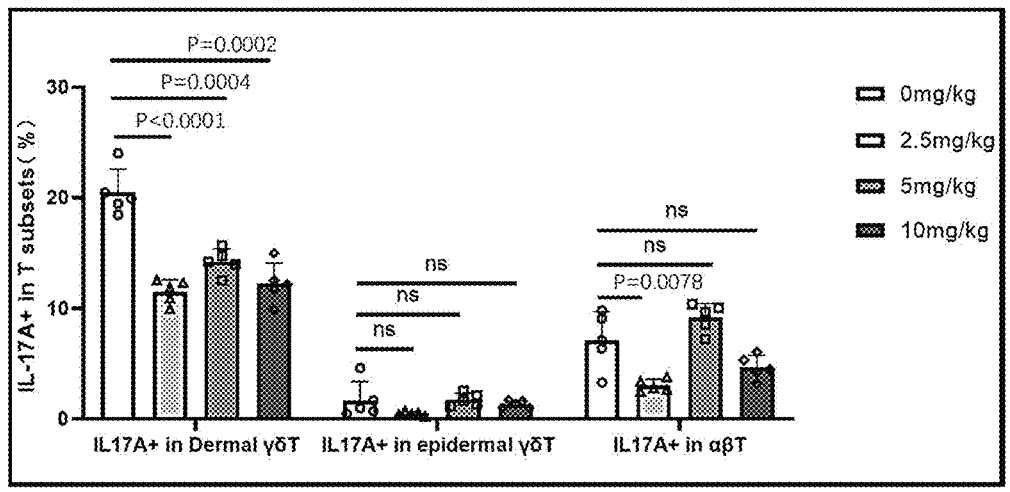
FIG. 15 illustrates results of skin of mice of respective treatment groups detected by flow cytometry.
Figure 16:
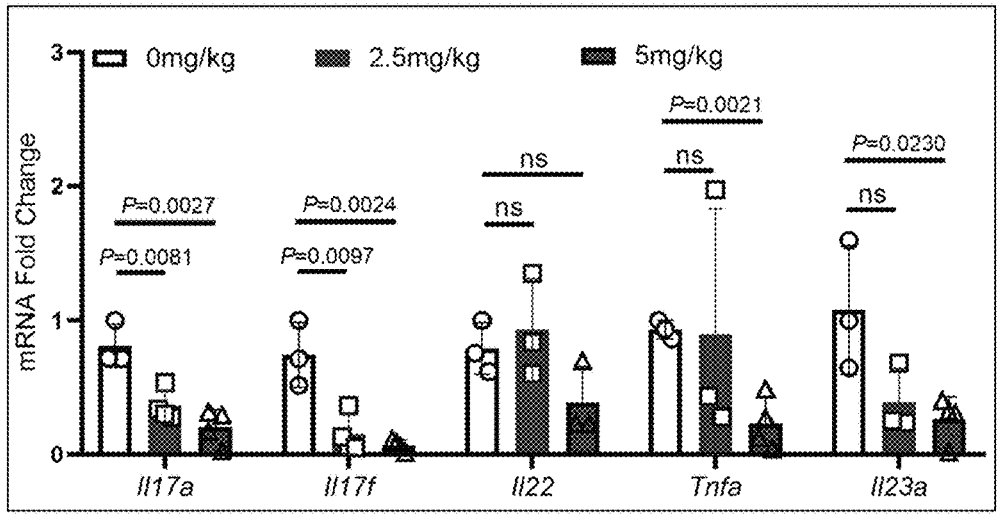
FIG. 16 illustrates results of skin of mice of respective treatment groups detected by quantitative polymerase chain reaction (qPCR).

The skin lymphocytes of mice in the above groups are isolated and detected by flow cytometry (i.e., the detection of the proportion of IL17A$^+$ cells in dermal γδT subsets, the IL17A$^+$ cells are main effector cells mediated by the CaMK2γ pathway of psoriasis and can secrete a large number of IL-17 cytokines to aggravate psoriasis). The results of flow cytometry are shown in FIG. 15. Compared with IMQ-induced mice without T2533, IMQ-induced mice treated with 5 mg/kg T2533 have the significantly reduced proportion of IL-17A$^+$ cells in dermal γδT subsets. Quantitative PCR is performed on known proinflammatory genes closely related to psoriasis, including Il17a, Il17f, Il22, Tnfa and Il23a. Results is shown in FIG. 16, the expressions of Il17a, Il17f, Tnfa and Il23a in the skin of mice treated with 5 mg/kg T2533 decrease significantly while the expression of Il22 is unchanged; and the expressions of Il17a and Il17f in the skin of mice treated with 2.5 mg/kg T2533 decrease significantly while the expressions of Il22, Tnfa and Il23a are unchanged.

Finally, the above embodiments are only used to illustrate the technical solution of the disclosure rather than limit it. Although the disclosure has been described in detail with reference to the preferred embodiments, it should be understood by those skilled in the art that the technical solution of the disclosure can be modified or replaced equivalently without departing from the spirit and scope of the technical solution of the disclosure, which should be included within the scope of appended claims of the disclosure.

What is claimed is:

1. A method of treating psoriasis, comprising:
administering a compound or a pharmaceutical derivative thereof in combination with a biological agent targeting a downstream molecule interleukin (IL)-17 or a downstream molecule IL-23 to patients with psoriasis at a target dosage of 5 milligrams per kilogram (mg/kg) body weight of the compound or the pharmaceutical derivative thereof per day within a treatment period to inhibit calcium/calmodulin-dependent protein kinase type II gamma (CaMK2γ) protein activity, and making the compound or the pharmaceutical derivative thereof act at an upstream of a CaMK2γ pathway for binding inhibition in the patients with psoriasis, wherein the compound ($C_{19}H_{21}N_3O$) is shown in a formula I, and the formula I is expressed as follows:

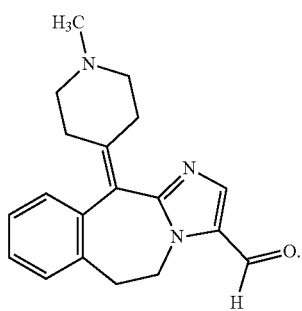

formula I

2. The method according to claim 1, wherein the compound is in a form of a pharmaceutical salt.

3. The method according to claim 2, wherein the compound is in a form of a pharmaceutical acid addition salt.

4. A use of a compound or a pharmaceutical derivative thereof, comprising:
dissolving powder of the compound or the pharmaceutical derivative thereof with dimethyl sulfoxide (DMSO) and then diluting with β-cyclodextrin to prepare a drug with a target dosage for inhibiting CaMK2γ protein activity, wherein the compound is as shown in a formula I, and the formula I is expressed as follows:

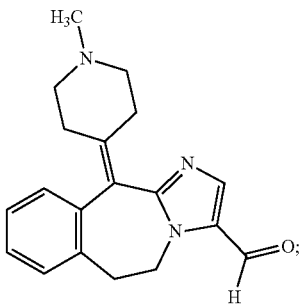

formula I wherein the drug is configured to be administered to a patient with psoriasis at the target dosage per day within a treatment period to treat the psoriasis and the target dosage is 5 mg/kg body weight of the compound or the pharmaceutical derivative thereof.

5. The use according to claim 4, wherein the drug for inhibiting the CaMK2γ protein activity is specifically used to inhibit the CaMK2γ protein activity in psoriatic tissues.

6. The use according to claim 5, wherein the compound is in a form of a pharmaceutical salt.

7. The use according to claim 6, wherein the compound is in a form of a pharmaceutical acid addition salt.

8. The use according to claim 4, wherein a dosage form of the drug for inhibiting the CaMK2γ protein activity is at least one selected from a group consisting of a capsule, a tablet, an oral preparation, a microcapsule preparation, an injection, a suppository, a spray, and an ointment.

9. The use according to claim 5, wherein a dosage form of the drug for inhibiting the CaMK2γ protein activity is at least one selected from a group consisting of a capsule, a tablet, an oral preparation, a microcapsule preparation, an injection, a suppository, a spray, and an ointment.

10. The use according to claim 6, wherein a dosage form of the drug for inhibiting the CaMK2γ protein activity is at least one selected from a group consisting of a capsule, a tablet, an oral preparation, a microcapsule preparation, an injection, a suppository, a spray, and an ointment.

11. The use according to claim 7, wherein a dosage form of the drug for inhibiting the CaMK2γ protein activity is at least one selected from a group consisting of a capsule, a tablet, an oral preparation, a microcapsule preparation, an injection, a suppository, a spray, and an ointment.

* * * * *